US007384387B1

(12) United States Patent  
Raillard et al.

(10) Patent No.: US 7,384,387 B1
(45) Date of Patent: Jun. 10, 2008

(54) HIGH THROUGHPUT MASS SPECTROMETRY

(75) Inventors: Sun Ai Raillard, Mountain View, CA (US); Yong Hong Chen, Foster City, CA (US); Claus Krebber, Palo Alto, CA (US); Jeremy Minshull, Los Altos, CA (US); Willem P. C. Stemmer, Los Gatos, CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/502,283

(22) Filed: Feb. 11, 2000

Related U.S. Application Data

(60) Provisional application No. 60/119,766, filed on Feb. 11, 1999, provisional application No. 60/148,848, filed on Aug. 12, 1999.

(51) Int. Cl.
    *C40B 30/10*  (2006.01)
(52) U.S. Cl. .......................... 506/12; 250/283; 250/288; 250/292
(58) Field of Classification Search .................. 435/6, 435/7.1
    See application file for complete search history.

(56) References Cited

U.S. PATENT DOCUMENTS

| | | | |
|---|---|---|---|
| 4,683,202 A | 7/1987 | Mullis | |
| 5,417,923 A | 5/1995 | Bojanic et al. | |
| 5,426,039 A | 6/1995 | Wallace et al. | |
| 5,512,463 A | 4/1996 | Stemmer | |
| 5,514,588 A | 5/1996 | Varadaraj | |
| 5,605,793 A | 2/1997 | Stemmer | |
| 5,756,316 A | 5/1998 | Schellenberger | |
| 5,763,239 A | 6/1998 | Short et al. | |
| 5,770,860 A | 6/1998 | Franzen | |
| 5,783,431 A | 7/1998 | Peterson et al. | |
| 5,789,228 A | 8/1998 | Lam et al. | |
| 5,811,238 A | 9/1998 | Stemmer et al. | |
| 5,814,473 A | 9/1998 | Warren et al. | |
| 5,824,469 A | 10/1998 | Horwitz et al. | |
| 5,824,485 A | 10/1998 | Thompson et al. | |
| 5,830,696 A | 11/1998 | Short | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,866,363 A | 2/1999 | Pieczenik | |
| 5,876,997 A | 3/1999 | Kretz | |
| 5,925,749 A | 7/1999 | Mathur et al. | |
| 5,928,905 A | 7/1999 | Stemmer et al. | |
| 5,939,250 A | 8/1999 | Short | |
| 5,939,300 A | 8/1999 | Robertson et al. | |
| 5,942,430 A | 8/1999 | Robertson et al. | |
| 5,948,666 A | 9/1999 | Callen et al. | |
| 5,958,672 A | 9/1999 | Short | |
| 5,958,751 A | 9/1999 | Murphy et al. | |
| 5,962,258 A | 10/1999 | Mathur et al. | |
| 5,962,283 A | 10/1999 | Warren et al. | |
| 5,965,408 A | 10/1999 | Short | |
| 5,985,646 A | 11/1999 | Murphy et al. | |
| 6,001,574 A | 12/1999 | Short et al. | |
| 6,004,788 A | 12/1999 | Short | |
| 6,030,779 A | 2/2000 | Short | |
| 6,054,267 A | 4/2000 | Short | |
| 6,083,761 A | 7/2000 | Kedar et al. | |
| 6,146,854 A | 11/2000 | Koster et al. | |
| 6,258,605 B1 * | 7/2001 | Chace | 436/86 |
| 6,274,088 B1 | 8/2001 | Burbaum et al. | |
| 6,322,970 B1 * | 11/2001 | Little et al. | 435/6 |
| 6,340,588 B1 | 1/2002 | Nova et al. | |
| 6,500,617 B1 * | 12/2002 | Stemmer et al. | 435/6 |
| 2002/0076739 A1 * | 6/2002 | Aebersold et al. | 435/7.92 |

FOREIGN PATENT DOCUMENTS

| | | |
|---|---|---|
| EP | 0911396 A2 | 4/1999 |
| EP | 911396 A3 | 5/1999 |
| EP | 934999 A1 | 8/1999 |
| WO | WO 92/12233 | 7/1992 |
| WO | WO 94/16101 | 7/1994 |
| WO | 9522625 A1 | 8/1995 |
| WO | 9633207 A1 | 10/1996 |

(Continued)

OTHER PUBLICATIONS

Siuzdak, G. Mass Spectrometry for Biotechnology. New York: Academic Press. 1992.*
Fabretto et al. "MS/MS applications in biological problems" Mass Spectrometry Reviews 1993, 12, 313-395.*
Carter, Paul (1985) "Improved Oligonucleotide-Mutagenesis Using M13 Vectors" *Annu. Rev. Genet. Methods in Enzymology* vol. 154 pp. 382-403.
Chang et al., *Nature Biotechnology* (1999) vol. 17, pp. 793-797.
Chauvaux N., et al. *Journal of Chromatography* (1997) vol. 775, No. 1-2, abstract only.
Christians et al., (1999) Directed evolution of thymidine kinase for AZT phosphorylation using DNA family shuffling *Nature Biotechnology* 17:259-264.
Crameri et al., 1994, "Combinatorial Mutiple Cassette Mutagensesis Creates all the Permutations of Mutant and Wild-Type Sequences." *Biotech.* p. 194-197.

(Continued)

*Primary Examiner*—Jon D. Epperson
(74) *Attorney, Agent, or Firm*—Sharon M. Fujita; Stacy Landry; Norman J. Kruse

(57) ABSTRACT

Apparatus and methods for high throughput mass spectrometry are provided. The methods involve sample preparation in an off-line parallel purification system. Such methods include but are not limited to the use of an appropriate buffer when generating samples or the use of a solid support for tagged components. The samples prepared in this way do not then need to be column separated. The apparatus provided includes a cell growth plate for growing cells and generating products and/or reactants, an off-line parallel purification system, a mass spectrometer, and an automatic sampler that transports samples and injects them into the mass spectrometer of the apparatus. The methods and apparatus described are used, for example, in screening enzyme reaction pathways.

26 Claims, 5 Drawing Sheets

FOREIGN PATENT DOCUMENTS

| | | |
|---|---|---|
| WO | WO97/07205 | 2/1997 |
| WO | WO97/20078 | 6/1997 |
| WO | WO97/25410 | 7/1997 |
| WO | WO97/35957 | 10/1997 |
| WO | WO97/35966 | 10/1997 |
| WO | WO97/44361 | 11/1997 |
| WO | WO97/48416 | 12/1997 |
| WO | WO97/48717 | 12/1997 |
| WO | WO97/48794 | 12/1997 |
| WO | WO98/00526 | 1/1998 |
| WO | WO98/01581 | 1/1998 |
| WO | WO98/13485 | 4/1998 |
| WO | WO98/13487 | 4/1998 |
| WO | WO98/15969 * | 4/1998 |
| WO | WO 98/20020 | 5/1998 |
| WO | WO98/24799 | 6/1998 |
| WO | WO98/27230 | 6/1998 |
| WO | WO98/28416 | 7/1998 |
| WO | WO98/31837 | 7/1998 |
| WO | WO98/36080 | 8/1998 |
| WO | WO98/41622 | 9/1998 |
| WO | WO98/41623 | 9/1998 |
| WO | WO98/41653 | 9/1998 |
| WO | 9842727 A1 | 10/1998 |
| WO | WO98/42832 | 10/1998 |
| WO | WO98/48034 | 10/1998 |
| WO | WO98/58085 | 12/1998 |
| WO | WO99/07837 | 2/1999 |
| WO | WO99/08539 | 2/1999 |
| WO | WO99/10472 | 3/1999 |
| WO | WO99/10539 | 3/1999 |
| WO | WO99/19518 | 4/1999 |
| WO | WO99/21979 | 5/1999 |
| WO | WO99/23107 | 5/1999 |
| WO | WO99/23236 | 5/1999 |
| WO | 99/41369 | 8/1999 |
| WO | WO99/41368 | 8/1999 |
| WO | WO99/41383 | 8/1999 |
| WO | WO99/41402 | 8/1999 |
| WO | WO99/45154 | 9/1999 |
| WO | WO99/57128 | 11/1999 |
| WO | WO99/65927 | 12/1999 |
| WO | WO 00/37684 | 6/2000 |

OTHER PUBLICATIONS

Crameri et al., 1996. "Construction and evolution of antibody-phage libraries by DNA shuffling." p. 100-102.

Crameri et al., 1996, "Improved Green Fluorescent Protein by Molecular Evolution Using DNA Shuffling." *Nature Biotechnology.* vol. 14 : p. 315-319.

Crameri et al., 1997. "Molecular evolution of an arsenate detoxification pathway by DNA shuffling." *Nature Biotechnology.* vol. 15: p. 436-438.

Crameri et al., 1998. "DNA shuffling of a Family of Genes from diverse species accelerates directed evolution." *Nature.* vol. 391: p. 288-291.

Gates et al., 1995. "Affinity Selective Isolation of Ligands from Peptide Lidaries Through Display on a lac Repressor 'Headpiece Dimer.'" *J. Mol. Biol.* p. 1-14.

Grundstrom et al. (1985) "Oligonucleotide-directed Mutagenesis by Microscale 'Shot-gun' Gene Synthesis." *Nucleic Acids Research* vol. 13, No. 9:p. 3305-3315.

Kramer & Fritz (1987) "Oligonucleotide-Directed Construction of Mutations via Gapped Duplex DNA" *Methods in Enzymology* vol. 154 pp 350-367.

Kramer et al. (1984) "Different Base/Base Mismatches Are Corrected with Different Efficiencies by the Methyl-Directed DNA Mismatch-Repair System of *E. coli.*" Cell vol. 38: p. 879-887.

Kunkel, Thomas A. (1985) "Rapid and efficient site-specific mutagenesis without phenotypic selection" *Proc. Matl. Acad. Sci. USA* vol. 82 pp. 488-492.

Minshull and Stemmer (1999) "Protein evolution by molecular breeding" *Current Opinion in Chem. Biol.* 3:284-290.

Ness et al., (1999) "DNA shuffling of subgenomic sequences of subtilisin" *Nature Biotechnology* 17:893-896.

Patten et al., (1997) "Applications of DNA shuffling to pharmaceuticals and vaccines" *Current Opinion in Biotech.* 8:724-733.

Sakmar et al. (1988) "Total Synthesis and Expression of a Gene for the α-subunit of Bovine Rod Outer Segment Guanine Nucleotide-binding Protein (transducin)." *Nucleic Acids Research* 16Vol. 16, No.14:p. 6361-6372.

Stemmer et al., 1995. "Single-step assembly of a gene and entire plasmid from large numbers of oligodeoxynucleotides." vol. 164: p. 49-53.

Stemmer, "Sexual PCR and Assembly PCR." p. 447-458.

Stemmer, 1994, "DNA shuffling by random fragmentation and reassembly: In vitro recombination for molecular evolution." *Proc. Natl. Acad. Sci. USA.* vol. 91: pp. 10747-10751.

Stemmer, 1994. "Rapid evolution of a protein in vitro by DNA shuffling." Nature. vol. 370 No. 4: p. 389-391.

Stemmer, 1995. "Searching Sequence Space." *Bio/Technology.* vol. 13: p. 549-553.

Stemmer, 1995, "The Evolution of Molecular Computation." vol. 270: p. 1510.

Weinmann et al., *J. of Analytical Toxicology* vol. 22 (1998) pp. 319-328.

Wu et al., *Chemistry & Biology* vol. 4, No. 9 pp 653-657.

Zhang et al., 1997. "Directed evolution of a fucosidase from a galactosidase by DNA shuffling and screening." *Proc. Natl. Acad. Sci. USA.* vol. 94: p. 4504-4509.

Dongre, A.R., et al., *Tibtech* (1997) 15:418-425.

Kaye, B., et al., *Anal. Chem.* (1996) 68:1658-1660.

Simpson, H., et al., *Rapid Commun. In Mass Spectrometry* (1998) 12:75-82.

International Search Report for PCT/US00/03686.

Chauvaux, N. et al., (1997). Quantative Analysis of 1-aminocyclopropane-1-carboxylic acid by liquid chromatography coupled to electrospray tandem mass spectrometry. In Journal of Chromatography (vol. 775, pp. 143-150), New York, NY, [abstract] by Biological Abstracts, Philadelphia, PA, Abstract No. PREV199799712581, Lines 14-16 XP0022142054.

Kato, K. et al, (1997). Rapid characterization of urinary metabolitesof pibutidine hydrochloride in humans by lliquid chromatography/electrospray ionization tandem mass spectrometry. In Rapid Communucations in Mass Spectrometry (vol. 13(15), pp. 1626-1632) London UK, [abstract] by Medline, Washington DC, Abstract No. 9935217, Lines 9-11, XP002142053.

Weinmann, W. et al. (1998). Fast screening for drugs of abuse by solid-phase extraction combined with flow-injection ionspray-tandem mass spectrometry. In Journal of Analytical Toxicology (vol. 22(4) pp. 319-328), New York NY, [abstract] by chemical Abstracts, 129(17), Abstract No. 212610, XP002142055.

Ostermeier et al. (1999) "A combinatorial approach to hybrid enzymes independent of DNA homology" *Nature Biotech*17:1205.

Arnhelm et al., "Polymerase Chain Reaction," C&EN 36-47 (Oct. 1990).

Barringer et al., "Blunt-end and single-strand ligations by escherichia coli ligase: influence on an in vitro amplification scheme," Gene 89:117-122 (1990).

Botstein et al., "Strategies and applications of in vitro mutagenesis," Science 229(4719):1193-1201 (Sep. 1985).

Carter, Paul, "Site-directed mutagenesis," Biochem J. 237:1-7 (1986).

Carter et al., "Improved oligonucleotide site-directed mutagenesis using M13 vectors," Nucleic Acids Research 13(12):4431-4443 (1985).

Cheng et al., "Long PCR," Nature 369:685-685 (Jun. 1994).

Crameri et al., "1020-Fold aptamerlibrary amplification without gel pruification," Nucleic Acids Research 21(18):4410 (1993).

Desouza et al., "Atrazine Chlorohydrolase from pseudomonas sp. strain ADP: Gene sequence, enzyme purification, and protein characterization," Journal of Bacteriology 178(16): 4894-4900 (Aug. 1996).

Fritz et al., "Oligonucleotide-directed construction of mutations: a gapped duplex DNA procedure without enzymatic reactions in vitro," Nucleic Acids Research 16(14):6987-6999 (1988).

Guatelli et al., "Isotherman, in vitro amplification of nucleic acids by a multienzyme reaction modeled after retroviral replication," Proc. Natl. Acad. Sci 87:1874-1878 (Mar. 1990).

Kramer, Wilfried et al., "Improved enzymatic in vitro reactions in the gapped duplex DNA approach to oligonucleotide-directed construction of mutations," Nucleic Acids Research 16(14):7207 (1988).

Kramer, Wilfried et al., "The gapped duplex DNA approach to oligonucleotide-directed mutation construction," Nucleic Acids Research 12(24):9441-9456 (1984).

Kunkel, Thomas A. et al., "Rapid and efficient site-specific mutagenesis without phenotypic selection," Methods in Enzymology 154:367-382 (1987).

Kunkel, Thomas A., "the efficiency of oligonucleotide-directed mutagenesis" in "Nucleic Acids and Molecular Biology," Eckstein and Lilley, eds. Springer Verlag, Berlin 2:124-135 (1988).

Kwoh et al., "Transcription-based amplification system and detection of amplified human immunodeficiency virus type 1 with a bead-based sandwich hybridization format," Proc. Natl. Acad. Sci. USA 86:1173-1177 (Feb. 1989).

Landergren Ulf et al., "A Ligase-mediated gene detection technique," Science 241:1077-1080 (Aug. 1988).

Nakamaye, Kay L., et al., "Inhibition of restriction endonuclease Nci I Cleavage by phosphorothioate groups and its application to oligonucleotide-directed mutagenesis," Nucleic Acids Research 14(24):9679-9698 (1986).

Ostermeier, Marc et al, "A combinatorial approach to hybrid enzymes independent of DNA homology," Nautre Biotechnology 17:1205-1209 (Dec. 1999).

Sayers, Jon R. et al., "Strand specific cleavage of phosphorothioate-containing DNA by reaction with restriction endonucleases in the presence of ethidium bromide," Nucleic Acids Research 16(3):803-814 (1988).

Sayers, Jon R. et al., "5'-3' exonucleases in phosphorothioate-based oligonucleotide-directed mutagenesis," Nucleic Acids Research 16(3):791-802 (1988).

Schatz, Peter J., "Use of peptide libraries to map the substrate specificity of a peptide-modifying enzyme: a 13 residue consensus peptide specifies biotinylation in escherichia coli," Biotechnology 11:1138-1143 (Oct. 1993).

Smith, Paul A. et al., "A plasmid expression system for quantitative in vivo biotinylation of thioredoxin fusion proteins in Escherichia coli," Nucleic Acids Research 26(6):1414-1420 (1998).

Smith, Michael et al., "In vitro Mutagenesis," Ann. Rev. Genet 19:423-62 (1985).

Sooknanan et al., "NASBA: A Detection and amplification system uniquely suited for RNA," Biotechnology 13:563:564 (Jun. 1995).

Stemmer et al., "Molecular breeding of viruses for targeting and other clinical properties," Tumor Targeting 4:1-4 (1999).

Taylor, John et al., "The use of phosphorothioate-modified DNA in restriction enzyme reactions to prepare nicked DNA," Nucleic Acids Research 13(24):8749-8764 (1985).

Taylor, John et al., "The rapid generation of oligonucleotide-directed mutations at high frequency using phosphorothioate-modified DNA," Nucleic Acids Research 13(24):8765-8785 (1985).

Van Brunt, Jennifer, " Amplifying genes: PCR and its alternatives," Bio/Technology 8:291-294 (Apr. 1990).

Wells, James A. et al., "Cassette mutagenesis: an efficient method for generation of multiple mutations at defined sites," Gene 34:315-323 (1985).

Wu, Dan Y. et al., "Specificity of the nick-closing activity of bacteriophage T4 DNA ligase," Gene 76:245-254 (1989).

Zoller, Mark J. et al., "Oligonucleotide-directed mutagenesis of DNA fragments cloned into M13 vectors," Methods in Enzymology 100:468-500 (1983).

Zoller, Mark J. et al., "Oligonucleotide-directed mutagenesis: A simple method using two oligonucleotide primers and a single-stranded DNA template," Methods in enzymology 154:329-350 (1987).

Zoller, Mark J. et al., "Oligonucleotide-directed mutagenesis using M13-derived vectors: an efficient and general procedure for the production of point mutations in any fragment of DNA," Nucleic Acids Research 10(20):6487-6500 (1982).

* cited by examiner

HIGH THROUGHPUT MASS SPECTROMETRY

CROSS-REFERENCE TO RELATED APPLICATIONS

The present application claims benefit of and priority to U.S. Ser. No. 60/119,766, "High Throughput Mass Spectrometry," by Raillard, filed Feb. 11, 1999; U.S. Ser. No. 60/148,848 entitled "Evolution and Use of Enzymes for Combinatorial and Medicinal Chemistry," by Liu et al., filed Aug. 12, 1999.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention relates to high throughput methods for mass spectrometry, for example, to monitor a plurality of samples, e.g., enzyme products generated from a library, e.g., of gene sequences.

BACKGROUND OF THE INVENTION

High throughput chemical screening, of enzyme activity for example, typically involves quantitative detection of one or more substrate and/or product. The most universal detection method to date is mass spectrometry (MS), which allows identification of a particular organic molecule based on mass to charge ratio.

Traditionally, mass spectrometry is performed in tandem with liquid chromatography to purify and separate the components of interest. This purification can be considered to be on-line sequential purification. The sequential nature of the purification limits the ability of mass spectrometry to screen a large number of reaction products in a short amount of time, because the purification must occur in line with and previous to the mass spectrometry.

DNA shuffling technology is used to create a library of related gene sequences that encode, e.g., one or more enzyme that catalyzes a reaction. Such a library is constructed, e.g., by homologous exchange of DNA fragments during DNA shuffling.

In one typical set of embodiments, the library of related gene sequences is on a plasmid that has been transformed into a bacteria. Thus a single bacterial clone can carry a unique gene sequence representing a unique variant of a particular enzyme or enzyme pathway.

For directed evolution, the library is screened for variants having a desired characteristic. Evolution of enzymes and pathways involves biochemical reaction of one or more enzymes that can be detected by a chemical screening method. A chemical screening method detects the substrates and or products of the enzyme reaction(s).

Presently, the use of mass spectrometry to analyze these enzyme reactions is extremely time consuming. The time limitation is due to the need to separate and purify the products and reactants of the enzyme pathways before injection into a mass spectrometer. This limits the number of samples that can be analyzed to about 100 samples per day (typical purification runs (e.g., liquid chromatography) require about 10 minutes/sample. At 6 samples per hour, 144 samples can be run in a 24-hour period). A new high throughput system would be useful to provide a method of analyzing a library for a few mutants out of thousands that will provide the desired properties.

One recently developed system is the electrospray method as described in "Quantitative Electrospray Mass-Spectrometry for the Rapid Assay of Enzyme Inhibitors," by Wu et al. in *Chemistry & Biology* 1997, Vol. 4 No. 9, p653–657. Electrospray ionization is a mild method of transferring charged polar organic molecules into the gas phase for mass spectrometry analysis and is applicable for most biologically relevant organic molecules. The electrospray method eliminates the need for prior derivatization of samples before injection into a mass-spectrometer as in GC/MS and thus shortens the analysis time for mass spectrometry. However, column separation is still utilized in this technique, limiting throughput as noted above.

Another recent development is described in "Fast Screening for Drugs of Abuse by Solid-Phase Extraction Combined with Flow-Injection Ionspray-Tandem Mass Spectrometry," by Weinman and Svobodain, Journal of Analytical Toxicology, Vol. 22, 1998, p. 319–328. The technique described combined tandem mass spectrometry and electrospray methods to simultaneously detect different drugs in serum or urine. Although no column separation was used because the tandem mass spectrometry allowed detection of multiple compounds, a solid phase extraction method was necessary in the sample preparation. The sample preparation steps were still too lengthy to provide high throughput screening by mass spectrometry.

Accordingly, a high throughput method of performing mass spectrometry, e.g., for screening libraries of shuffled molecules, would be useful. The present invention fulfills these and many other needs which will become apparent upon complete review of this disclosure.

SUMMARY OF THE INVENTION

The invention provides a method for high throughput mass spectrometry, that is used, for example, to monitor enzyme reactions, e.g., at the rate of about 100 samples or more per hour, more preferably about 200 samples or more per hour. Using this method, many samples can be screened simultaneously so that an entire library can be screened in a week or less. This provides a faster method of mass spectrometry screening than has previously existed. The increase in throughput is due to a novel off-line parallel purification system. The off-line parallel purification eliminates the need for liquid chromatography or a separate purification step before injection of the sample into a mass spectrometer.

In one embodiment, a method of performing high throughput mass spectrometry screening is provided. In the method, one or more cells are grown. Non-column-separated components of interest are purified from the cell colony or culture. In one aspect, the purification includes an off-line parallel adjustment of cell growing conditions or attachment of the non-column-separated components to a solid support. In the method, flow-injection analysis is performed using, e.g., electrospray tandem mass spectrometry, thereby obtaining mass-to-charge ratio data and providing high throughput mass spectrometry screening of the non-column-separated components of interest.

The growing and purifying steps are achieved essentially simultaneously by adjusting growing conditions or the conditions used to produce the reactants or products of interest. For example, the components of interest can be produced from whole cells, from cell supernatant, from cell lysate or from purified enzymes with added substrates. This production occurs in a volatile buffer, a buffer that reduces concentration of ionic species followed by a purification/clean up method such as an ion exchange resin, or the production is modified to be compatible with extraction, e.g., with an organic solvent to provide a component that can be injected directly into the mass spectrometer with no further purification. Because these steps are in parallel, at least 100 cell colonies are screened for presence or activity of the one or more non-column-separated component in less than an hour.

Alternatively, the purifying step is achieved by lysing cells and attaching one or more components, e.g., tagged components such as tagged enzymes, proteins, or nucleic acids, to a solid support comprising, e.g., a tag binding moiety. The cell lysate is optionally washed from the solid support and the enzymes are contacted with one or more substrates, producing one or more products, which are optionally analyzed without further purification.

The one or more non-column-separated component is a protein, a protein binding molecule, a carbohydrate, a carbohydrate binding molecule, an enzyme, an enzyme substrate, a product of an enzyme catalyzed reaction, a nucleic acid, a product of a nucleic acid catalyzed reaction, a substrate with one or more hydrophobic moieties, an inorganic ion, an oligosaccharide, a hydrophobic molecule, a briatine derivative, atrazine, a polyketide, or other molecule of interest.

In another embodiment, the present invention provides a method for monitoring products or reactants, such as in enzyme reactions, by high throughput mass spectrometry by providing a cell or bacteria that has been transformed with a plasmid containing one or more member of a library, e.g., of related gene sequences, such as related enzyme gene sequences. One or more cells or a cell colony or culture is grown from the cell; producing one or more product or reactant from the cell colony or culture in a biological matrix, thereby producing a non-column-separated sample; purifying the non-column separated sample from the biological matrix using an off-line parallel adjustment of the biological matrix, and monitoring the non-column separated sample by flow-injection analysis using electrospray tandem mass spectrometry, thereby monitoring the one or more product or reactant. In this way, enzyme reactions and their products can be studied at high throughput levels.

The products and/or reactants can be purified simultaneous to production, thus providing an off-line parallel purification system. The products and/or reactants are produced, e.g., using whole cells, cell supernatant, cell lysate, or from a reaction between at least one purified cell enzyme and at least one substrate. The components of the sample are optionally a substrate with one or more hydrophobic moieties, an inorganic ion, a small molecule, an oligosaccharide, a hydrophobic molecule, a peptide, a polypeptide, a protein, a nucleic acid, a polynucleotide, a hydrophilic molecule, a triazine derivative, a secondary metabolite such as a polyketide, a protein, a protein binding molecule, a carbohydrate, a carbohydrate binding molecule, an enzyme, an enzyme substrate, a product of an enzyme catalyzed reaction, a nucleic acid, a product of a nucleic acid catalyzed reaction, or the like. The components are optionally known or unknown components. Unknown components are optionally identified and/or quantified using mass spectrometry analysis.

The purifying system, which typically occurs in reaction conditions that mimic environmental cellular conditions, comprises altering or adding a buffer to the biological matrix in which the non-column-separated sample is produced, thereby producing a sample that can be injected directly into a mass spectrometer for analysis of the sample. The buffer used is optionally a volatile buffer, a buffer that reduces concentration of ionic species, a buffer that allows easy parallel off-line purification such as an ion exchange resin, or an organic solvent extraction. Alternatively, the purifying system comprises binding an enzyme or other component, e.g., a nucleic acid, protein, peptide, carbohydrate, or the like, to a solid support, e.g., through a specific tag moiety. Reactions are then performed on the solid support, which is optionally washed to remove impurities or unbound components, thereby producing samples that are sufficiently purified for injection into a mass spectrometer. Using one of these purification techniques, at least about 100 library members or more are screened for presence or absence of products or reactants in less than an hour. Typically, at least about 200 or more library members are screened in about an hour. Preferably, at least about 500 or more samples are screened in about an hour.

In other embodiments, throughput is optionally increased, e.g., by pooling samples or components and injecting the pooled samples into the mass spectrometer for simultaneous analysis. The resulting data is typically deconvoluted, e.g., using fragmentation patterns or spectra, to identify the different samples.

In another embodiment, this invention provides an apparatus for high throughput mass spectrometry screening. The apparatus comprises a cell growth plate for growing cell samples and reacting enzymes, enzyme substrates, and enzyme products; an off-line parallel purification system coupled to or within the cell growth plate, for purifying the samples; an automatic sampler coupled to the off-line parallel purification system; and a mass spectrometer, such as an electrospray triple quadrupole tandem mass spectrometer, coupled to the automatic sampler. The automatic sampler is a sample handler that transports samples from the off-line parallel purification system to the mass spectrometer for injection and analysis. It can transport, e.g., at least 100 samples or more in about an hour.

Using the apparatus and integrated systems of the invention, the rate of screening is determined by the maximum rate at which the automatic sampler transports samples between the off-line purification system and the mass spectrometer. This is due to the ability of the apparatus to purify the samples for injection in an off-line parallel system, that is optionally a volatile buffer, a buffer that reduces concentration of ionic species, an ion exchange resin, an organic solvent, or a solid support, e.g., to bind an enzyme or other component.

In another aspect, the apparatus of the invention comprises a computer and software operably coupled to the apparatus for recording and analyzing mass spectrometer data and for controlling the automatic sampler.

DEFINITIONS

Figure 1:
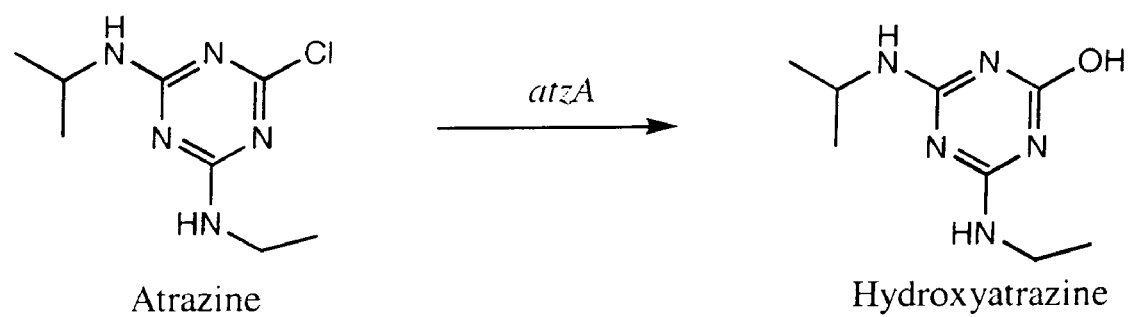
FIG. 1 shows the enzymatic conversion of atrazine to hydroxyatrazine by atzA.

The term "non-column-separated component" refers to components or materials of interest, e.g., that are injected into a mass spectrometer, without prior in-line sequential separation, e.g., on a chromatography column. Without a sequential in-line separation, the components are optionally analyzed in a high throughput system. Parallel systems that allow components to be purified or separated as they are produced allow high throughput analysis.

In the present invention the term "off-line parallel adjustment of cell growing conditions" or "off-line parallel purification system" or "off-line parallel adjustment of biological matrix" is used to refer to a new method of sample preparation. The method is used to prepare complex samples for injection into a mass spectrometer without a time-consuming sequential purification and/or separation step. In this method, the samples and their reaction conditions are adjusted or modulated, e.g., in a cell growth plate in parallel with the production of products and reactants of interest. Cell growing conditions and reaction conditions are optimized, e.g., to obtain products with sufficient purity for, e.g., mass spectrometry, by routine alteration and optimization of reaction parameters and conditions. The system is not coupled to a column separation system that functions in line with and sequential to the mass spectrometer. In one embodiment, the non-column separated components are purified without separation. Alternatively, the offline purification system comprises a reactor, e.g., an enzyme reactor, e.g., a solid support for binding or attaching a library of components, e.g., tagged enzymes are optionally bound to a solid support comprising tag-binding molecules. For example, cells that have been transformed with genes encoding enzyme sequences with specific tags, e.g., biotin, are typically lysed after expression of the enzyme. The enzymes are bound to the support or enzyme reactor, e.g., a solid support comprising streptavidin, and the cell lysate is optionally removed, e.g., by removing the solid support from the cell lysate or by filtering the cell lysate from the solid support. Substrates are provided to perform enzyme reactions on the support, thereby producing products that are sufficiently pure for injection into a mass spectrometer. The solid support optionally comprises a set of magnetic, agarose, or polystyrene beads, pins, a membrane, or the like. For example, beads are optionally placed in a sample well, e.g., on a cell growth plate. When the cells are lysed, tagged components bind to the beads, e.g., via a tag-binding moiety on the beads. The beads are then optionally removed from the sample well for further reaction or identification. Alternatively, the cell lysate is removed or washed from the beads. Pins are optionally lifted in and out of a sample well to bind to and/or remove tagged components from a sample. Similarly, a membrane is optionally used to bind components. Other non-tagged components are optionally washed from the membrane or the membrane is removed, e.g., from the sample well to provide purified components.

"Product or reactant" is used herein to refer to products or reactants, e.g., of enzyme catalyzed reactions. The product or reactant is optionally a protein, a peptide, a protein or peptide binding molecule, a carbohydrate, a carbohydrate binding molecule, a nucleic acid molecule, a polynucleotide, a nucleic acid or polynucleotide binding molecule, or a product of a nucleic acid catalyzed reaction. Additionally, the product and or reactant is optionally an enzyme or enzyme substrate. The product or reactant is any molecule of interest that is to be analyzed by the methods of the invention.

A "cell growth plate" is used herein to refer to a plate on which cells can be grown in an appropriate media. Exemplar plates include 1536, 384 or 96-well microtiter plates. The plates are used to grow cell colonies. For example cell colonies containing gene libraries are picked directly from transformation plates into 1536, 384 or 96-well microtiter plates with appropriate growth media using, for example, a Q-bot from Genetix. Additionally, the off-line parallel purification and/or adjustment of reaction conditions occurs on the cell growth plate when the products or reactants of interest are generated. All product generation and purification steps optionally occur in the wells of the cell growth plate. In some embodiments, the cell growth plate comprises a solid support, e.g., particles, beads, a membrane, a set of pins, or the like, for binding one or more components, e.g., enzymes, e.g., after cells are lysed. For example, each well of a microtiter plate optionally comprises one or more agarose beads, e.g., beads comprising avidin or streptavidin to which enzymes comprising a biotin tag will bind. Alternatively, a set of pins is optionally introduced into the wells of the cell growth plate to bind to or remove tagged enzymes from the cell lysate.

A "mass spectrometer" is an analytical instrument that can be used to determine the molecular weights of various substances, such as proteins and nucleic acids. It can also be used in some applications, e.g., to determine the sequence of protein molecules and the chemical composition of virtually any material. Typically, a mass spectrometer comprises four parts: a sample inlet, an ionization source, a mass analyzer, and a detector. A sample is optionally introduced via various types of inlets, e.g., solid probe, GC, or LC, in gas, liquid, or solid phase. The sample is then typically ionized in the ionization source to form one or more ions. The resulting ions are introduced into and manipulated by the mass analyzer. Surviving ions are detected based on mass to charge ratio. In one embodiment, the mass spectrometer bombards the substance under investigation with an electron beam and quantitatively records the result as a spectrum of positive and negative ion fragments. Separation of the ion fragments is on the basis of mass to charge ratio of the ions. If all the ions are singly charged, this separation is essentially based on mass. A quadrupole mass spectrometer uses four electric poles for the mass analyzer. These techniques are described generally in many basic texts, e.g., Quadrupole Mass Spectrometry and its Applications, by Peter Dawson, Springer Verlag, 1995; and Spectrometric Identification of Organic Compounds, by Silverstein, Bassler and Morrill, Fourth Edition, 1981. In an electrospray mass spectrometry system, ionization occurs by an electric field that is used to generate charged droplets and subsequent analyte ions by ion evaporation for TIS analysis. See, Richard B. Cole (1997) "Electrospray Ionization Mass Spectrometry" John Wiley and Sons, Inc.

"High throughput mass spectrometry" is used herein to refer to a mass spectrometry system that is capable of screening samples at a rate of from about 100 or 200 samples per day to about 15,000 samples per day. In the present invention, systems are provided that screen about 200 samples in less than an hour, e.g., 200 samples are injected into a mass spectrometer and analyzed in less than an hour. In addition, high throughput mass spectrometry refers to the pooling of samples, e.g., into a single injection. For example, multiple samples are pooled into a single injection. This increases the rate of screening of the mass spectrometer because multiple samples are simultaneously injected. About 2 to about 1000 samples are optionally pooled. Typically about 5 to about 500 samples are pooled or about 5 to about 100 samples. In other embodiments, about 5 to about 20 samples are pooled. For example, 100 samples are optionally pooled into a single injection and 200 injections are optionally made in about an hour, thereby screening a total of 20,000 samples by MS in about an hour. In other words, samples, e.g., clones or library members, are screened at a rate of about 480,000 samples per day. This is well over the typical MS screening rate of about 100 to about 200 samples per day. A "high throughput system" typically has throughput rates as described above. Systems of interest in the present case, include, but are not limited to, mass spectrometry systems, magnetic resonance systems, IR and UV spectroscopy systems, and the like.

A "cell colony" is used herein to refer to the in vitro propagation of cells isolated from living tissues. A cell colony, as used herein, is typically a growth of cells on a solid medium or in a liquid culture, typically one that is visible to the eye without magnification. The one or more cells or clones (cells having the same genetic makeup) from a cell colony may be analyzed as whole cells or in the form of a complete cell lysate or a cell supernatant. A purified cell lysate is the product of cell lysis or the complete or partial disintegration or breaking up of the cell wall. The cells may be lysed before use in the present invention and the resulting cell lysate used to generate the products or reactants of interest. Alternatively, the cell supernatant is used to generate components of interest. For interest secreted proteins are optionally obtained or purified from cell supernatant and used in the methods of the invention.

As used herein, "purified cell enzymes with added substrates" refers to enzymes that have been previously purified from cells or other sources. Substrates are then added to the purified enzymes to produce reaction products of interest. This is in contrast to the generation of reaction products from whole cells or cell lysates. When the purified enzymes are attached to a solid support, e.g., an enzyme reactor, the reaction products are optionally purified by washing the solid support or by removal of the enzymes from the reaction mixture, e.g., by removal of the solid support. For example when enzymes are purified from a cell lysate using pins comprising a tag-binding moiety, the pins are optionally placed into a reaction mixture for the enzyme reaction and then removed at the conclusion of the reaction, leaving behind a purified product.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidites, methyl phosphonates, chiral-methyl phosphonates, 2-O-methyl ribonucleotides, peptide-nucleic acids (PNAs).

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, "product of an enzyme catalyzed reaction" refers to any product generated by a reaction that has been catalyzed by an enzyme. Enzymes react with substrate molecules to produce reaction products that are of interest in the present invention. For example, to evolve a new functional enzyme, the identity and detection of products of the new enzyme's reaction with substrates will provide important information regarding the functionality of the new enzyme. The products are optionally known compounds or unknown compounds.

As used herein, "product of a nucleic acid catalyzed reaction" refers to any product generated by a reaction that has been catalyzed by a nucleic acid functioning as an enzyme, e.g., the cleavage product of a hammerhead or hairpin ribozyme.

The term "protein binding molecule" is used herein to refer to any molecule which binds or interacts with a protein. It includes, but is not limited to, other proteins, carbohydrates, lipids, nucleic acids and the like.

The term "carbohydrate" includes any of a large class of carbon-hydrogen-oxygen compounds. It includes but is not limited to sugars and their polymers, e.g., starch, glycogen, glucose, and cellulose, and polyhydroxyaldehydes, polyhydroxyketones, or their derivatives. Most but not all carbohydrates are represented chemically by the formula, $C_x(H_2O)_n$, where "n" is three or higher.

"Carbohydrate binding molecule" is used herein to refer to any molecule or compound that binds or interacts with a carbohydrate, either specifically or non-specifically. It includes but is not limited to other carbohydrates, proteins, lipids, nucleic acids and the like.

The term "enzyme," as used herein, generally refers to a protein which acts as a catalyst to reduce the activation energy of a chemical reaction in other compounds or "substrates."

The term "substrate with one or more hydrophobic moieties" is used herein to refer to a substrate that comprises a molecule that has at least one, and possibly more, hydrophobic group or portion.

An "inorganic ion" is an ion which does not comprise an organic component.

"Oligosaccharide" refers to a relatively short molecular chain made up of about 10 to about 100 simple sugars or monosaccharide units.

The term "hydrophobic molecule" refers to any molecule or portion of a molecule which has an affinity for oil at an oil-water interface. A "hydrophilic molecule" refers to molecule or any portion of a molecule that has an affinity for water at an oil-water interface.

The term "library" is used herein to refer to gene libraries, e.g., produced by mutagenesis, recombination, directed evolution, shuffling, or other diversity generating techniques; enzyme libraries; combinatorial or chemical libraries; naturally occurring libraries; e.g., of microorganisms; libraries of non-biological compounds, and the like. "Library of related gene sequences" is used herein to refer to a group of similar gene sequences, for example gene sequences encoding enzymes or enzyme subunits that have been evolved or shuffled to create new and/or related genes that encode enzymes with the ability to act on a new substrate, or for enhanced catalytic properties with an old substrate, either alone or in combination with other genes. In some embodiments, a library comprises a group of genes that have been fused to a sequence encoding a specific tag, e.g., a biotin tag. For example, the expression products of such a library are then optionally bound to a solid support comprising a tag-binding moiety, e.g., avidin or streptavidin, that binds the specific tag.

As used herein, "biological matrix" refers to the fluid, substance, or reaction mixture or growth medium in which a cell is grown. The products and reactants of interest in the invention are optionally generated and/or purified in the biological matrix. The biological matrix is typically similar to the native environmental conditions of the enzyme or substance of interest. In some embodiments, the enzymes, e.g., tagged enzymes, are removed from the biological matrix by binding to a solid support, e.g., polystyrene or magnetic beads in a cell growth plate or pins dipped into the wells in which the cells were grown and lysed.

"Transformed" as used herein, refers to a cell that has been transfected or transduced with a nucleic acid. A cell has been "transformed" by an exogenous nucleic acid when such exogenous nucleic acid has been introduced inside the cell membrane. Exogenous DNA may or may not be integrated (covalently linked) into chromosomal DNA making up the genome of the cell. The exogenous DNA may be maintained on an episomal element, such as a plasmid. Transformation refers to any way of getting a nucleic acid across a cell membrane, including electroporation, ballistics, injection, using lipid-nucleic acid complexes, etc.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

A "plasmid" is a DNA molecule with an origin of replication. The plasmid is capable of being replicated in one or more host cell types. Because a plasmid is usually small and relatively simple, they are commonly used in recombinant DNA experiments as acceptors of foreign DNA.

The term "simultaneously" refers to two events that occur at essentially the same time. For example, the generation of the products or reactants of interest in the present invention occurs simultaneously with the purification in the off-line parallel purification system. The two events are both done at the same time in the same location, e.g., the cell growth plate, to save time in the analysis, thus allowing a high throughput mass spectrometry screening to occur.

An "automatic sampler" is a robotic handler that transports samples from one location to another. An automatic sampler is used for example, to transport samples from a cell growth plate and inject them into a mass spectrometer for analysis. Examples of automatic samplers include the Gilson 8-probe microtiter autosampler and the microtiter autosampler from CTC analytics. Automatic samplers optionally include robotic handlers that are used to pick colonies, such as a Q-bot, and/or add or remove reagents to or from the cell growth plate.

DETAILED DISCUSSION

Mass spectrometry has been used to detect metabolites in biological fluids and to monitor enzyme reactions. See, e.g., "Quantitative Electrospray Mass Spectrometry for the Rapid Assay of Enzyme Inhibitors. Wu et al., Chemistry and Biology, Sep. 19, 1997, 4, p653. In one embodiment, the present invention uses the inherent capacity of electrospray MS to monitor enzyme reactions and their reaction products by adapting a high throughput flow injection analysis. Using the method of the present invention, a sample is injected directly into a mass spectrometer without any column separation and analyzed instantly. The speed of the analysis is limited only by the motoric movements of the autosampler used to inject the samples. Thus, an entire 96-well microtiter plate of samples is typically run in less than an hour. Autosampler companies, such as Gilson and CTC Analytics are currently working to increase the throughput to one plate in 10 minutes, which would then allow for about 570 injections per hour or about 13,000 injections into a mass spectrometer in a day. If samples are pooled, e.g., about 2 to about 1000 samples are combined and injected simultaneously, then the screening rate increases to about 1000 samples per hour to about 575,000 samples per hour or about 25,000 samples per day to about 13 million samples or more per day.

One aspect of the present mass spectrometry method is that the samples are purified off-line so that an in-line sequential chromatography step is not necessary. A liquid chromatography (LC) step, to separate the components, is usually coupled to the mass spectrometer (MS) in a sequential fashion so that the limiting factor in mass spectrometry throughput is the speed at which the LC can process components. With an off-line purification system, such as the one herein, the speed of mass spectrometry analysis is not limited by a sequential purification step. The mass spectrometry throughput in this invention is typically rate dependent on how fast the automatic sampler can transport and inject the samples into the mass spectrometer.

To analyze enzyme reactions using high-throughput mass spectrometry, first a single colony of cells must be picked and grown. Second, enzyme products are generated using whole cells, complete or partial cell lysates, or purified enzymes to which substrates have been added. Third, the products generated from the biological matrix are purified in an off-line parallel purification system. Fourth, flow injection analysis is performed using tandem mass spectrometry.

Applications for high-throughput MS include but are not limited to screening plasma, urine or cerebral spinal fluid, or the like for, i.e., identification of metabolites that correlate with cancer susceptibility or presence, event specific testing of exposure to toxins, monitoring effects of drug trials, monitoring effects of prescribed drug use, creation of a metabolite encyclopedia that contains metabolite profiles for every type of cell in the human body. Additionally, testing and analysis can be performed on non-human animals, plants, and food and drink items, such as grain or wine. In another aspect, high throughput (HTP) MS is used in plant genetics for identification of the gene pathways responsible for synthesis of commercially valuable plant products, such as drugs, and oils, and for identification of the effects of gene transformation on metabolite phenotype, or for screening plants for the presence of desired natural products. High-throughput MS is also useful for similar analyses in bacterial and viral systems. In a particularly useful aspect of present invention, high throughput mass spectrometry (HTP-MS) is used to screen libraries of cells, e.g., for an expression product of a shuffled nucleic acid or for screening a library for enzyme activity e.g., a library produced from directed evolution or shuffling.

I. Integrated System Elements
  Making Libraries

The present invention typically utilizes DNA shuffling or directed evolution technologies to make libraries which are screened by the high throughput methods of the invention, but other types of libraries are also available and are optionally screened by the present methods. A "library" of compositions or compounds in the present invention is a large collection of samples, e.g., composed of proteins, expression products, genes, nucleic acids, cells, pharmacologically active compositions, e.g., drugs, small organic molecules, peptides, and the like. Libraries include, but are not limited to, a library of biological or chemical compositions, such as a library of expression products or variant genes or a library of mutagenized cells. Such libraries are optionally generated by DNA shuffling, random mutagenesis, transposon mutagenesis, or combinatorial gene assembly. Gene libraries are optionally expressed to produce libraries of expression products which are screened by MS. The present methods are optionally uses to screen any desired group of compounds or molecules. Techniques for the production of libraries are well known to those of skill in the art.

Making libraries typically includes the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well known to persons of skill. General texts which describe molecular biological techniques useful herein, including mutagenesis, include Berger and Kimmel, *Guide to Molecular Cloning Techniques Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). Examples of techniques sufficient to direct persons of skill through in vitro amplification methods (useful for making library nucleic acids), including the polymerase chain reaction (PCR) the ligase chain reaction (LCR), Q-replicase amplification and other RNA polymerase mediated techniques (e.g., NASBA) are found in Berger, Sambrook, and Ausubel, id., as well as in Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Methods of transducing cells, including plant and animal cells, with nucleic acids as in library construction are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley-Liss, New York (1994)) and the references cited therein, Humason (*Animal Tissue Techniques*, fourth edition W.H. Freeman and Company (1979)) and Ricciardelli, et al., *In Vitro Cell Dev. Biol.* 25:1016–1024 (1989). References for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg N.Y.) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS).

A variety of diversity generating/product screening reactions are optionally used to produce libraries that are optionally screened by the methods provided herein. For example libraries of related enzyme encoding genes are optionally expressed and the products of the enzyme reactions purified and analyzed in a high throughput format by mass spectroscopy as described herein. One important class of such diversity generating reactions is so called "nucleic acid shuffling" or "DNA shuffling". In these methods, any of a variety of recombination-based diversity generating procedures can be used to diversify starting nucleic acids, or organisms comprising nucleic acids, or even to diversify character strings which are "in silico" (in computer) representations of nucleic acids. Diverse nucleic acids/character strings/organisms which are generated are typically screened for one or more activity. Nucleic acids, character strings, or organisms which comprise nucleic acids are then used as substrates in subsequent recombination reactions, the products of which are, again, screened for one or more activity. This process is repeated recursively until one or more desirable product is produced.

A variety of diversity generating protocols, including nucleic acid shuffling protocols, is available and fully described in the art. The following publications describe a variety of recursive recombination procedures and/or methods which can be incorporated into such procedures, as well as other diversity generating protocols: Stemmer, et al., (1999) "Molecular breeding of viruses for targeting and other clinical properties. Tumor Targeting" 4:1–4; Nesset et al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" Nature 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proceedings of the National Academy of Sciences, U.S.A.* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" Nature Medicine 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'" *Journal of Molecular Biology* 255:373–386; Stemmer (1996) "Sexual PCR and Assembly PCR" In: The Encyclopedia of Molecular Biology. VCH Publishers, New York. pp. 447–457; Crameri and Stemmer (1995) "Combinatorial multiple cassette mutagenesis creates all the permutations of mutant and wild-type cassettes" *BioTechniques* 18:194–195; Stemmer et al., (1995) "Single-step assembly of a gene and entire plasmid form large numbers of oligodeoxyribonucleotides" *Gene*, 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proceedings of the National Academy of Sciences, U.S.A.* 91:10747–10751.

Additional details regarding DNA shuffling and other diversity generating methods are found in U.S. Patents by the inventors and their co-workers, including: U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;" U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "METHODS AND COMPOSITIONS FOR CELLULAR AND METABOLIC ENGINEERING."

In addition, details and formats for DNA shuffling and other diversity generating protocols are found in a variety of PCT and foreign patent application publications, including: Stemmer and Crameri, "DNA MUTAGENESIS BY RANDOM FRAGMENTATION AND REASEMBLY" WO 95/22625; Stemmer and Lipschutz "END COMPLEMENTARY POLYMERASE CHAIN REACTION" WO 96/33207; Stemmer and Crameri "METHODS FOR GENERATING POLYNUCLEOTIDES HAVING DESIRED CHARACTERISTICS BY ITERATIVE SELECTION AND RECOMBINATION" WO 97/0078; Minshul and Stemmer, "METHODS AND COMPOSITIONS FOR CELLULAR AND METABOLIC ENGINEERING" WO 97/35966; Punnonen et al. "TARGETING OF GENETIC VACCINE VECTORS" WO 99/41402; Punnonen et al. "ANTIGEN LIBRARY IMMUNIZATION" WO 99/41383; Punnonen et al. "GENETIC VACCINE VECTOR ENGINEERING" WO 99/41369; Punnonen et al. OPTIMIZATION OF IMMUNOMODULATORY PROPERTIES OF GENETIC VACCINES WO 9941368; Stemmer and Crameri, "DNA MUTAGENESIS BY RANDOM FRAGMENTATION AND REASSEMBLY" EP 0934999; Stemmer "EVOLVING CELLULAR DNA UPTAKE BY RECURSIVE SEQUENCE RECOMBINATION" EP 0932670; Stemmer et al., "MODIFICATION OF VIRUS TROPISM AND HOST RANGE BY VIRAL GENOME SHUFFLING" WO 9923107; Apt et al., "HUMAN PAPILLOMAVIRUS VECTORS" WO 9921979; Del Cardayre et al. "EVOLUTION OF WHOLE CELLS AND ORGANISMS BY RECURSIVE SEQUENCE RECOMBINATION" WO 9831837; Patten and Stemmer, "METHODS AND COMPOSITIONS FOR POLYPEPTIDE ENGINEERING" WO 9827230; Stemmer et al., and "METHODS FOR OPTIMIZATION OF GENE THERAPY BY RECURSIVE SEQUENCE SHUFFLING AND SELECTION" WO9813487.

Certain U.S. Applications provide additional details regarding DNA shuffling and related techniques, as well as other diversity generating methods, including "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, U.S. Ser. No. 09/407,800; "EVOLUTION OF WHOLE CELLS AND ORGANISMS BY RECURSIVE SEQUENCE RECOMBINATION", by del Cardyre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392, and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393, and "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118,854) and U.S. Ser. No. 09/416,375 filed Oct. 12, 1999.

As review of the foregoing publications, patents, published applications and U.S. patent applications reveals, recursive recombination of nucleic acids to provide new nucleic acids with desired properties can be carried out by a number of established methods and these procedures can be combined with any of a variety of other diversity generating methods, e.g., to produce libraries that are optionally screened as described herein.

In brief, at least 5 different general classes of recombination methods are applicable to the present invention and set forth in the references above. First, nucleic acids can be recombined in vitro by any of a variety of techniques discussed in the references above, including e.g., DNAse digestion of nucleic acids to be recombined followed by ligation and/or PCR reassembly of the nucleic acids. Second, nucleic acids can be recursively recombined in vivo, e.g., by allowing recombination to occur between nucleic acids in cells. Third, whole genome recombination methods can be used in which whole genomes of cells or other organisms are recombined, optionally including spiking of the genomic recombination mixtures with desired library components. Fourth, synthetic recombination methods can be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made by tri-nucleotide synthetic approaches. Fifth, in silico methods of recombination can be effected in which genetic algorithms are used in a computer to recombine sequence strings which correspond to nucleic acid homologues (or even non-homologous sequences). The resulting recombined sequence strings are optionally converted into nucleic acids by synthesis of nucleic acids which correspond to the recombined sequences, e.g., in concert with oligonucleotide synthesis/gene reassembly techniques. Any of the preceding general recombination formats can be practiced in a reiterative fashion to generate a more diverse set of recombinant nucleic acids, which are optionally screened using the purification and MS methods provided herein.

The above references provide these and other basic recombination formats as well as many modifications of these formats. Regardless of the format which is used, the nucleic acids of the invention can be recombined (with each other or with related (or even unrelated) to produce a diverse set of recombinant nucleic acids, including, e.g., sets of homologous nucleic acids.

DNA shuffling provides a robust, widely applicable, means of generating diversity useful for the engineering of proteins, pathways, cells and organisms with improved characteristics. In addition to the basic formats described above, it is sometimes desirable to combine shuffling methodologies with other techniques for generating diversity. In conjunction with (or separately from) shuffling methods, a variety of diversity generation methods can be practiced and the results (i.e., diverse populations of nucleic acids) screened for in the systems of the invention. Additional diversity can be introduced by methods which result in the alteration of individual nucleotides or groups of contiguous or non-contiguous nucleotides, i.e., mutagenesis methods. Mutagenesis methods include, for example, recombination (PCT/US98/05223; Publ. No. WO98/42727); oligonucleotide-directed mutagenesis (for review see, Smith, *Ann. Rev. Genet.* 19: 423–462 (1985); Botstein and Shortle, Science 229: 1193–1201 (1985); Carter, *Biochem. J.* 237: 1–7 (1986); Kunkel, "The efficiency of oligonucleotide directed mutagenesis" in *Nucleic acids &Molecular Biology*, Eckstein and Lilley, eds., Springer Verlag, Berlin (1987)). Included among these methods are oligonucleotide-directed mutagenesis (Zoller and Smith, *Nucl. Acids Res.* 10: 6487–6500 (1982), *Methods in Enzymol.* 100: 468–500 (1983), and *Methods in Enzymol.* 154: 329–350 (1987)) phosphothioate-modified DNA mutagenesis (Taylor et al., *Nucl. Acids Res.* 13: 8749–8764 (1985); Taylor et al., *Nucl. Acids Res.* 13: 8765–8787 (1985); Nakamaye and Eckstein, *Nucl. Acids Res.* 14: 9679–9698 (1986); Sayers et al., *Nucl. Acids Res.* 16:791–802 (1988); Sayers et al., *Nucl. Acids Res.* 16: 803–814 (1988)), mutagenesis using uracil-containing templates (Kunkel, *Proc. Nat'l. Acad. Sci. USA* 82: 488–492 (1985) and Kunkel et al., *Methods in Enzymol.* 154:367–382)); mutagenesis using gapped duplex DNA (Kramer et al., *Nucl. Acids Res.* 12: 9441–9456 (1984); Kramer and Fritz, *Methods in Enzymol.* 154:350–367 (1987); Kramer et al., *Nucl. Acids Res.* 16: 7207 (1988)); and Fritz et al., *Nucl. Acids Res.* 16: 6987–6999 (1988)). Additional suitable methods include point mismatch repair (Kramer et al., *Cell* 38: 879–887 (1984)), mutagenesis using repair-deficient host strains (Carter et al., *Nucl. Acids Res.* 13: 4431–4443 (1985); Carter, *Methods in Enzymol.* 154: 382–403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415–423 (1986)), mutagenesis by total gene synthesis (Nambiar et al., *Science* 223: 1299–1301 (1984); Sakamar and Khorana, *Nucl. Acids Res.* 14: 6361–6372 (1988); Wells et al., *Gene* 34:315–323 (1985); and Grundström et al., *Nucl. Acids Res.* 13: 3305–3316 (1985). Kits for mutagenesis are commercially available (e.g., Bio-Rad, Amersham International, Anglian Biotechnology).

Following recombination, any nucleic acids which are produced are optionally selected for a desired activity. In the context of the present invention, this can include testing for and identifying any activity that can be detected in an automatable format, by any of the assays in the art. A variety of related (or even unrelated) properties can be assayed using any available assay and then screened, e.g., using high throughput MS.

In addition, any of the described shuffling techniques can be used in conjunction with procedures which introduce additional diversity into a genome or library. Example methods are described in Schellenberger U.S. Pat. No. 5,756,316, describing chimeric nucleic acid multimers; and in U.S. Pat. No. 5,965,408 describing chain termination methods of diversity generation. In addition, diversity can be further increased by using methods which are not homology based. For example, incremental truncation for the creation of hybrid enzymes (ITCHY) described in Ostermeier et al. (1999) "A combinatorial approach to hybrid enzymes independent of DNA homology" *Nature Biotech* 17:1205, can be used to generate an initial recombinant library which serves as a substrate for one or more rounds of in vitro or in vivo shuffling methods. Methods for generating and using multi-species expression libraries have been described, e.g., in U.S. Pat. Nos. 5,783,431; 5,824,485.

Any of these diversity generating methods can be combined with each other or with shuffling reactions, in any combination selected by the user, to produce nucleic acid diversity, which may be screened for using any available screening method. For example, a library of diverse nucleic acids is optionally expressed and the components of interest purified and screened by high throughput MS as described herein.

Cell Growth Plates

The cell growth plates of the invention are optionally 1536, 384 or 96-well microtiter plates, or the like. For example cell colonies containing gene libraries are picked directly from transformation plates into 1536, 384 or 96-well microtiter plates containing appropriate growth media using, for example, a Q-bot from Genetix. The maximum speed of the Q-bot is about 4000 colonies per hour.

The microtiter plates are typically incubated in a plate shaker for cell growth, e.g., typically for 1 day to about 2 weeks depending on the organism. Media and cell growth conditions are appropriate to the particular cells which are incubated.

The cell growth plate is also used for product generation when, for example, enzyme reactions are being studied. Products of reactions between enzymes and substrates are of interest when evolving new functional enzymes. These products and or the reactants should be analyzed in a high-throughput method so that many members of the enzyme gene library can be analyzed in a short period of time. To allow high-throughput measurement of the products and reactants, the products are optionally generated as part of the automated system of the invention. Therefore, any product generation steps that must be undertaken in the assay are optionally performed on the cell growth plate. After generation of products, the samples, e.g., the products and/or reactants, are optionally purified for injection into a mass spectrometer for analysis.

Off-Line Purification System

The off-line parallel purification system of the invention allows high-throughput mass spectrometry analysis because it allows the samples to be purified in a system that is not sequentially tied to and slowing down the mass spectrometry analysis. The system allows for off-line parallel purification of the products and/or reactants with no time-consuming column separation.

The off-line parallel purification of the invention is performed as part of the product generation on the cell growth plate. In this way the system allows all samples to be sufficiently purified for mass spectrometry analysis without a column separation that is performed sequentially and in-line with the mass spectrometer. To do this the system provides a chemical purification step that is selected based on the type of sample, e.g., reactant and/or product, analyzed. Furthermore, this chemical purification step can be performed in the wells of the cell growth plate in the off-line system of the invention.

For example, the off-line chemical purification step optionally comprises the use of a different or additional buffer when generating the products and/or reactants of interest. Alternatively, the off-line parallel purification system comprises the use of an ion exchange resin when generating the reactants and/or products of interest. By thus preparing the sample as it is produced, the system of the invention takes no additional time for purifying and/or separating the components to be analyzed.

Alternatively, the purification system comprises a component reactor, e.g., an enzyme reactor, that produces purified products for direct injection into a mass spectrometer. A component reactor, as used herein, refers to a solid support which is used to remove components of interest from a cell lysate or to remove a cell lysate from the components of interest, e.g., by attaching the components to the solid support. Components of interest, include, but are not limited to, nucleic acids, polynucleotides, proteins, polypeptides, enzymes, carbohydrates, lipids, and the like. For example, proteins, enzymes, peptides, or the like that have been tagged, e.g., by fusing a sequence for a specific tag to the gene that encodes, e.g., the enzyme, peptide, or protein, are optionally purified and immobilized on the solid support, e.g., in a specific and stable manner, thus forming, e.g., an enzyme reactor. Typically, the enzymes, proteins, or peptides are removed from a cell lysate by binding the tagged enzymes to a tag binding moiety immobilized on the solid support. For example, enzymes or other proteins are expressed in cells and the cells are lysed, e.g., using EDTA, lysozyme, DTT, PMBS, heat, sonication, or the like. If secreted proteins are the component of interest, no lysis is necessary. Other library components are also optionally tagged with a molecule that will bind the solid support. For example, biotin is optionally added chemically or enzymatically to any library component of interest, e.g., a nucleic acid, carbohydrate or small organic molecule.

The tagged components are then exposed to a tag binding matrix or solid support comprising a tag binding moiety. Examples of tag binding molecules and corresponding tags are provided below. The tag binding matrix or solid support typically comprises a tag binding moiety, e.g., a molecule that binds to the specific tag on the enzyme, and a solid matrix material. Optional solid supports include, but are not limited to, dispensable beads or particles, e.g., agarose, polystyrene, or magnetic beads, membranes, microwell plates or pins. The tagged enzymes or proteins bind to the tag binding moiety on the solid support. The unbound material is either dispensed or centrifuged or sucked away, e.g., in the case of beads or membranes. Magnetic beads are optionally separated from the unbound fraction by magnets, e.g., that remove the beads and the tagged enzymes from the cell lysate. Pins are typically lifted in and out of the lysate wells, e.g., in the cell growth plate. The use of pins optionally provides especially high throughput because the purification takes so little time. Washing is optionally performed after removal of the unbound material, in an analogous fashion. The solid support is washed with, e.g., a buffer, before performing reactions.

The tagged component immobilized on the solid support, e.g., in a purified and stable format, thereby provides a reactor, e.g., an enzyme reactor. Reactions are optionally carried out on the solid support and the tagged components, e.g., tagged enzymes, are easily removed after the reaction, e.g., by lifting the set of pins, to which the tagged components are bound, out of a reaction well. The removal of the tagged components leaves behind a purified product, e.g., that is optionally injected directly into a mass spectrometer, IR or NMR spectrometer, or the like without further purification or decontamination. Alternative methods of detection of the results include measurement of chromogenic or fluorogenic substrates and/or products.

One extremely stable interaction that is optionally used to provide a reactor as described above utilizes the binding of biotin to avidin or biotin to streptavidin. Avidin and streptavidin are optionally immobilized on a variety of solid supports available from a variety of suppliers, e.g., magnetic beads, agarose beads, or membranes. An enzyme is typically biotinylated in vivo by genetically fusing a special peptide tag to the N- or C-terminus of the enzyme while expressing the protein. See, e.g., Schatz (1993) Biotechnology 11, 1138–1143. The biotin-holoenzyme ligase recognizes those N- or C-terminal peptides as substrates and biotinylates a lysine residue in that peptide. The level of expression of these new substrates for the biotin-holoenzyme ligase is so high typically that not all molecules are biotinylated. Overexpression of the birA gene and addition of small amounts of biotin to the expression medium circumvents this problem. See, e.g., Smith et al. (1998) Nucleic Acids Res. 26, 1414–1420. Because of overexpression of the recombinant enzyme the amount of BCCP bound in the reactor is neglected or BCCP knockouts are optionally constructed for expression of the enzyme bio-tag fusions. Many variations on the theme of purification and immobilization of components of interest, e.g., enzymes, proteins, nucleic acids, or the like, will be evident upon further review by those of skill of the art.

Additional pairs of compounds useful for tagging include, but are not limited to, biotin and streptavidin, biotin and avidin, maltose binding protein and amylose; His-Tag Oligohis at the N- or C-terminus using immobilized metal chelate chromatography with NTA, IDA, TED, and the like as chelators; glutathione-S-transferase and reduced glutathione; strep-tag short artificial streptavidin binding tag and streptavidin, epitope tags, such as E-tag, myc-tag, HAG-tag, His-tag, and the like with monoclonal antibodies; chitin binding domain and chitin; S-tag and RNAse minus S-peptide mutant; cellulose binding proteins with cellulose domains; thioredoxin and DsbA with Thiobond; hexa-arginine poly-cation-tag with a polyanion column material; IGg and other IGg derived peptides with ProteinA or ProteinG minimized peptides; calmodulin binding peptide with calmodulin; and histactophilin with IMAC (immobilized metal chelate chromatography).

In one embodiment, a library of genes is provided, which genes encode one or more tagged enzymes. For example, a sequence for biotin is fused to an enzyme sequence to express a tagged enzyme, e.g., in cells. The cells are optionally lysed and the enzymes are typically bound to a tag-binding moiety on a solid support, e.g., a reactor. The enzymes are then optionally removed and reacted with substrates, e.g., purified substrates. The products produced in this manner are then pure enough for analysis, e.g., by mass spectroscopy or another high throughput system. Alternatively, the enzymes are reacted with substrates in the cell lysate and then removed. In another embodiment, the component of interest is a secreted protein. In this case, the protein is optionally removed from the cell supernatant, e.g., using a solid support reactor as described herein, for further reaction or analysis. In addition, the cell supernatant is optionally removed for use in further reactions.

The reactor as described above is optionally used multiple times, e.g., using the same or different substrates or reaction conditions, because it is optionally removed from the reaction upon completion, e.g., washed, and reused. This is especially useful when enzyme libraries are screened for novel activities and matching substrates are identified.

The reactors or solid supports of the present invention enable the use of purified enzymes, e.g., in activity assays, and results in a reusable system that is optionally used with multiple different substrates at different times, thereby providing an enzyme reactor, e.g., for chemical processing and engineering. Alternatively, the reactor is used with multiple different substrates at the same time because the reacted sample does not have to be purified before injection into a mass spectrometer. Additional details regarding solid support reactors is found in U.S. Ser. No. 60/148,848, "Evolution and Use of Enzymes for Combinatorial and Medicinal Chemistry," by Liu et al., filed Aug. 12, 1999.

Autosampler

An autosampler is coupled with the apparatus of the invention to transport samples between the cell growth plate, where cells are grown and reactants and/or products of interest are generated and purified, to the mass spectrometer for injection and analysis. Autosamplers can be purchased from standard laboratory equipment suppliers such as Gilson and CTC Analytics. Such samplers function at rates of about 10 seconds/sample to about 1 min/sample.

In addition, robotic sampler handlers are optionally used to pick cell colonies into the cell growth plate and add reagents in the off-line parallel purification system. For the generation of common arrangements involving fluid transfer to or from microtiter plates, a fluid handling station is used. Such robotic handlers include but are not limited to those produced by Beckman instruments and Genetix (e.g., the Q-bot). In addition, several "off the shelf" fluid handling stations for performing such transfers are commercially available, including e.g., the Zymate systems from Zymark Corporation (Zymark Center, Hopkinton, Mass.; http://www.zymark.com/) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

Robotic sampler handlers are also optionally used to remove enzymes from a cell growth plate or enzyme reactor as described above. For example, a robotic handler is optionally used to lift a set of pins from a reaction well or to position a magnet to lift a set of magnetic beads from a cell growth beads, e.g., beads comprising a tagged enzyme.

Mass Spectrometer

A variety of mass spectrometer instruments are commercially available. For example, Micromass (U.K.) produces a variety of suitable instruments such as the Quattro LC (a compact triple stage quadrupole system optimized e.g., for API LC-MS-MS) which utilizes a dual stage orthogonal "Z" spray sampling technique. Other suitable triple stage quadrupole mass spectrometers (e.g., the "TSQ" spectrometer) are produced by the Finnigan Corporation.

II. Transforming cells

In one embodiment of the present invention a cell is provided that has been transformed with a plasmid containing one or more members of a library of related gene sequences. The library of related gene sequences is optionally created by a general method for recursive sequence recombination. For example, the method can begin with a gene encoding an enzyme or enzyme subunit and evolved for the ability to act on a new substrate, or for enhanced catalytic properties with an old substrate, either alone or in combination with other genes in a multistep pathway.

The term "gene" is used herein broadly to refer to any segment or sequence of DNA associated with a biological function. Genes are optionally obtained from a variety of sources, including cloning from a source of interest or synthesizing from known or predicted sequence information, and may include sequences designed to have desired parameters. The ability to use a new substrate can be assayed in some instances by the ability to grow on a substrate as a nutrient source. In other circumstances such ability can be assayed by decreased toxicity of a substrate for a host cell, hence allowing the host to grow in the presence of that substrate. Biosynthesis of new compounds, such as antibiotics, can be assayed similarly by growth of an indicator organism in the presence of the host expressing the evolved genes. For example, when an indicator organism used in an overlay of the host expressing the evolved gene(s), wherein the indicator organism is sensitive or expected to be sensitive to the desired antibiotic, growth of the indicator organism would be inhibited in a zone around the host cell or colony expressing the evolved gene(s).

The library can vary widely in size from 10 to more than $10^5$, $10^9$, $10^{12}$ members or more. In some embodiments, the starting segments and the recombinant libraries generated will include full length coding sequences and any essential regulatory sequences, such as a promoter and polyadenylation sequence, for enhanced expression. In other embodiments, the recombinant DNA segments in the library can be inserted into a common vector providing sequences necessary for expression before performing screening or selection. A library containing related genes that encode enzymes is optionally produced, e.g., by recombination of a plurality of related genes. The library is optionally an in vitro set of molecules or contained in a phage, cell or the like. In other embodiments, the library comprises a library of enzyme genes that have been fused to provide tagged enzymes. The library is then screened, for example by the high throughput mass spectrometry of the present invention, e.g., to detect an improved enzyme or a desired product.

Cells are then transfected or transformed with one or more of the above library members using standard technology well known to those of skill in the art. Basic texts disclosing the general methods of use in this invention include Sambrook, Ausubel and Berger, all supra.

III. Growing Cells

In general, any type of cell is optionally used as a recipient of evolved genes. Cells of particular interest include many bacterial cell types, both gram-negative and gram-positive, such as *Rhodococcus, Streptomyces*, Actinomycetes, *Corynebacterium, Penicillium, Bacillus, Escherichia coli, Pseudomonas, Salmonella*, and *Erwinia*. Cells of interest also include eukaryotic cells, particularly mammalian cells (e.g., mouse, hamster, primate, human), both cell lines and primary cultures. Such cells include stem cells, including embryonic stem cells, zygotes, fibroblasts, lymphocytes, Chinese hamster ovary (CHO), mouse fibroblasts (NIH3T3), kidney, liver, muscle, and skin cells. Other eukaryotic cells of interest include plant cells, such as maize, rice, wheat, cotton, soybean, sugarcane, tobacco, and *arabidopsis*; fish, algae, fungi (*Penicillium, Fusarium, Aspergillus*, Podospora, *Neurospora*), insects, yeasts (Picchia and *Saccharomyces*), and the like.

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. Particularly advantageous hosts are *E. coli, lactobacilli, Streptomyces*, Actinomycetes, and filamentous fungi.

In the present invention, single colonies of cells are picked directly from transformation plates into 1536, 384 or 96-well microtiter plates or cell growth plates with appropriate growth media, such as LB, using, e.g., a Q-bot from Genetix. The maximum speed of the Q-bot is about 4000 colonies per hour. The microtiter plates are typically incubated in a special plate shaker for cell growth.

Each single colony is grown up to uniformity (this is optionally achieved by automating the process, e.g., inoculum size and culture conditions, and providing temperature and humidity controlled incubators) in a single microtiter well on the cell growth plate. In one aspect, library members, e.g., cells, viral plaques, spores or the like, are separated on solid media to produce individual colonies or plaques. Using an automated colony picker (e.g., the Q-bot, Genetix, U.K.), colonies are identified, picked and 10,000 different mutants inoculated into 96 or 384 well microtiter dishes, that optionally contain about 2 or 3 glass balls/well, e.g., 3 mm glass balls. The Q-bot does not pick an entire colony, but rather inserts a pin through the center of the colony and exits with a small sampling of cells, (or mycelia) and spores (or viruses in plaque applications). The time the pin is in the colony, the number of dips to inoculate the culture medium, and the time the pin is in the medium each affect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtitre plates, if used, act to promote uniform aeration of cells and the dispersal of mycelial fragments similar to the blades of a fermenter. For example, *Streptomyces* tend to clump together during culture, but remain relatively homogenous in culture if glass beads are added during mixing.

IV. Generating Cell Components of Interest

In one embodiment of the invention, one or more cells or clones, or a cell colony is then treated in one of several ways to initiate product formation from, for example, enzyme reaction pathways of the cells. If enzyme or protein expression was purposely suppressed during cell growth, expression can be induced by removing the suppressor or by adding activator molecules.

Cells that contain active enzymes can be lysed and treated with permeabilizing agents to enable bulky and/or strongly ionic substrates to penetrate cell walls. This is especially critical for gram-negative bacteria like *E. coli*. Some cell components, e.g., enzymes or proteins, are secreted into the media (i.e., if expressed in gram-positive bacteria like *bacillus* with an appropriate signal sequence) in which case no extra treatment is necessary.

In some cases, the components of interest, e.g., enzymes, proteins, or nucleic acids, are optionally purified on a purification resin. Reagents, e.g., enzyme substrates, are added to the purified components of interest, thus providing purified components or products. The protein purification step eliminates a lot of sample preparation steps to follow. In some embodiments, a component of interest is purified using a component or enzyme reactor as described above. Reactions are optionally performed in such a reactor and the enzymes or components removed, e.g., by centrifugation or magnetization, to provide a purified product for analysis, e.g., by MS. Initiation of product formation is optionally achieved by inoculating the bacterial culture into a different medium. In all cases, the initiation of product formation is performed in a parallel 96 or 384-well format on the cell growth plate of the invention.

V. Sample Preparation by Off-Line Parallel Purification.

Two factors influence the quantitative detection of the analyte in a mass spectrometer. First, the impurities in the matrix can suppress or mask the signal. Second, mass spectrometers are highly sophisticated instruments that are not designed for handling crude samples. Strongly ionic buffers and macromolecules like DNA or proteins in the matrix will lead to reduction in signal and in the worst case to clogging of the machine. Therefore, sample cleanup is of the utmost importance.

The present invention provides high-throughput methods for assays, e.g., enzyme assays, with whole cells or partially or completely lysed cells. Instead of a chromatographic separation step, the samples are cleaned up with extraction methods to get rid of proteins, nucleic acids, general cell junk, and debris, such as by solid phase extractions or ethanol/methanol precipitation. The methods used are viable for many components, including but not limited to sugars, peptides, polynucleotides, small inorganic molecules, polyketides, beta-lactam antibiotics, triazine derivatives, and the like.

Traditionally, crude samples were cleaned on a liquid phase chromatography column prior to introducing them into a mass spectrometer. Liquid chromatography mass spectrometry (LC/MS) was probably the most common way to clean crude samples. However, each column run is time consuming (10–30 minutes per sample), limiting the speed of the analysis.

Flow injection analysis (FIA) is generally only limited by the speed of the autosampler, which ranges from about 30 to about 40 seconds per injection and getting faster as new models of autosamplers are manufactured. Sample preparation for FIA takes into account every step from cell growth to reaction or product formation to introduction into the mass spectrometer. One important factor is to adjust reaction conditions for product formation to accommodate MS compatibility as much as possible without compromising screening quality. Reaction or assay conditions are as close as possible to the real environmental conditions under which the products and/or reactants of interest will be used. For example, when enzyme pathways are at issue, the reaction conditions are as close as possible to the conditions under which the enzymes are used, e.g., to ensure that directed evolution of the enzymes leads to the desired mutant variants. For example, production media of polyketides in *Streptomyces* contains inexpensive components typically used in fermentors. In general, the conditions chosen are project dependent. One skilled in the art will understand both the relevant biology and the appropriate form of analytic measurement, and thus can select reaction conditions.

Once these conditions are defined, further sample cleanup is often unnecessary. Effective sample cleanup is dependent on the physico-chemical nature of the analyte as well as the matrix. However, all sample cleanup is optionally done on the cell growth plate in an off-line system in parallel with the MS analysis.

Several strategies are optionally employed to accommodate a variety of different analytes in biological matrices. For example, small molecule substrates of interest with hydrophobic moieties like atrazine can penetrate into *E. coli* cytoplasma without lysis of the cells. Using a volatile buffer like ammonium acetate allows a very simple cleanup. In one aspect, cells are centrifuged and the buffer added to the supernatant. Substrate is added and cell debris is filtered off in a parallel fashion.

In another embodiment, small inorganic ion analytes are often masked by coordinating metal ions. Reaction buffers for enzyme reactions with these analytes are optionally chosen to reduce the concentration of ionic species to a minimum, and the remaining cations are removed by cationic exchange resin.

In another aspect, an oligosaccharide is the analyte of interest. Oligosaccharides are cleaned up by removing all ionic species using a mixed ion exchange resin. *E. coli.* cells are partially lysed, and all cell debris, DNA and protein impurities are precipitated with ethanol and removed by filtration.

In another aspect, the product or reactant of interest is a hydrophobic molecule, such as a polyketide. Hydrophobic molecules are extracted from the aqueous phase by organic solvents that also remove ionic impurities.

In another aspect, cells are lysed and enzymes or other components of interest, such as peptides, nucleic acids, and the like, are attached to a solid support, e.g., an enzyme reactor as described above. The enzymes are optionally contacted by substrates on the solid support and then removed from the reaction upon completion, resulting in products that are sufficiently pure to be used directly in mass spectrometry without further purification such as liquid chromatography.

Another example of offline sample preparation comprises 96-well parallel solid phase extraction (SPE), in which a plurality of samples, e.g., about 96 or about 384 samples, are simultaneously loaded on to a solid phase extraction plate, e.g., a 96-well plate, e.g., from Waters Corp. Milford Mass. Unwanted components are washed from the plate, e.g., using one or more buffers or solvents. Components of interest are retained inside a column of the SPE plate and optionally eluted by a relative high strength solvent into a corresponding microwell plate, e.g., a 96-well plate. Samples prepared in this manner are sufficiently purified for injection into a mass spectrometer.

In all of the above cases, sample preparation was adopted to process 96 samples in parallel in a highly automated fashion, thereby ensuring that screening was only rate dependent on the speed of sequential analysis of the mass spectrometer. Additionally, these adjustments to growing conditions or generation solvents provide sufficient purification of the sample for injection into a mass spectrometer.

VI. Mass Spectrometry

Mass spectrometry is a generic method that allows detection of a large variety of different small molecule metabolites. Ionspray and electrospray mass spectrometry have been used in many different fields for the analysis of organic compounds and for characterization of biomacromolecules. It is however, usually coupled to a separation technique, such as high performance liquid chromatography or capillary zone electrophoresis, which is performed in-line with the mass spectrometry analysis. This slows down the rate of mass spectrometry and limits its use as a high-throughput method. For a general discussion of mass spectrometry theory and techniques, see, e.g., *Kirk-Othmer Encyclopedia of Chemical Technology*, Volume 15, Forth Edition, pages 1071–1094, and all references therein. See, also, *Mass Spectrometry for Biotechnology*, G Siuzdak, Academic Press, San Diego, Calif., 1996; *Electrospray Ionization Mass Spectrometry: Fundamentals, Instrumentation, and Applications*, R. Cole (Ed.), Wiley and Sons, 1997; *Mass Spectrometry for Chemists and Biochemists*, Johnstone et al., Cambridge University Press, 1996; *Mass Spectrometry: Principles and Applications*, Hoffman et al., Wiley and Sons, 1996; *Quadrupole Mass Spectrometry and its Applications*, Dawson (ed.), Springer Verlag, 1995; and *Advances in Mass Spectrometry*, Karjalainen et al. (eds.), Elsevier Science, 1998).

Electrospray methods are used instead of gas chromatography procedures because no prior derivatization is required to inject the sample. Flow injection analysis methods (FIA) with ionspray-ionization and tandem mass spectrometry further the ability of the present invention to perform high-throughput mass spectrometry analysis. The ionspray method allows the samples to be injected without prior derivatization and the tandem mass spectrometry (MS—MS) allows extremely high efficiency in the analysis. Therefore, no column separation is needed.

Electrospray ionization is a very mild ionization method that allows detection of molecules that are polar and large which are typically difficult to detect in GC-MS without prior derivatization. Modern electrospray mass spectrometers detect samples in femtomole quantities. Since a couple of microliters are injected, samples are optionally injected in nanomolar concentrations, attomolar concentrations or lower. Quantitation is very reproducible with standard errors ranging from 2%–5%.

Tandem mass spectrometry uses the fragmentation of precursor ions to fragment ions within a triple quadrupole MS. The separation of compounds with different molecular weights occurs in the first quadrupole by the selection of a precursor ion. The identification is performed by the isolation of a fragment ion after collision induced dissociation of the precursor ion in the second quadrupole. Reviews of this technique can be found in Kenneth, L. et al. (1988) "Techniques and Applications of Tandem Mass Spectrometry" VCH publishers, Inc.

Triple quadrupole mass spectrometers allow MS/MS analysis of samples. For example, a triple quadrupole mass spectrometer with electrospray and atmospheric pressure chemical ionization sources, such as a Finnigan TSQ 7000, is optionally used. The machine is optionally set to allow one particular parent ion through the first quadrupole which undergoes fragmentation reactions with an inert gas. The most prominent daughter ion can then be singled out in the third quadrupole. This method creates two checkpoints for analyte identification. The particle must have the correct molecular mass to charge ratio of both parent and daughter ion. Tandem mass spectrometry thus leads to higher specificity and often also to higher signal to noise ratio. It also introduces further separation by distinguishing analyte from impurities with same mass to charge ratio.

Other techniques of use in the present invention include, but are not limited to, neutral loss and parent ion scanning. Neutral loss is a method of mass spectrometry scanning in which all compounds that lose a neutral molecular fragment, i.e., a specific neutral fragment, during collision induced dissociation (CID) are detected. Parent ion mode detects all compounds that produce a common daughter ion fragment during CID. These techniques are optionally used, e.g., to quantitate the amount of product and starting material simultaneously. For systems in which the expected product is not known, e.g., a standard is not available, the neutral loss and/or parent ion method allows backtracking or deconvolution based on fragmentation patterns to determine the structure and/or identity of the starting material. For example, the parent mass is determined based on the various fragments produced. This is especially useful for detecting novel enzyme activity when the product of the enzyme reaction is not known, but is predictable.

In neutral loss methods, components of interest are allowed to pass the first quadrupole, e.g., in a triple quadrupole spectrometer, one at a time by scanning the first quadrupole in a certain mass range. The components, e.g., ions, are fragmented in the second mass filter by CID. If a specific neutral fragment is lost from a parent ion during the CID process, a daughter ion is formed, which daughter ion has a mass equal to the mass of the parent ion minus the mass of the neutral molecule. The daughter ion will pass the third filter and be detected. In this way, any ion or components losing a neutral fragment, e.g., a constant neutral fragment ($N_0$) during the CID process in the second quadrupole is optionally detected by scanning the first and third quadrupoles simultaneously with a mass offset equal to the mass $N_0$.

In the parent ion method, ions or components of interest are allowed to pass the first quadrupole one at a time. These ions are fragmented in a second mass filter by CID. The third quadrupole is then set to allow only specific ions to pass. Thus, all components, e.g., products or reactants, producing a specific fragment ion as set in the second quadrupole are detected by scanning the first quadrupole mass filters in the range of interest while setting the third quadrupole mass filter on that specific ion.

The speed of the analysis is limited only by the motoric movements of the autosampler used to inject the samples, such as a CTC Analytics and Gilson, Inc. Middleton, Wis. The speed for example, is optionally set at 30 seconds without wash and 40 seconds with wash of the injection needle. Such a sampling rate allows 2880 samples per day to be analyzed by MS if automated overnight runs are used. Thus, an entire 96-well microtitre plate of samples is run in less than an hour. Preferably, the speed of the autosampler is set at about 15 seconds per sample, allowing about 5000 samples to be screened in one day or about 200 per hour. Autosampler companies are currently working to increase the throughput to one plate in 10 minutes including the washing, which would then allow for about 8500 MS samples to be run in a day.

With the above mass spectrometry system and the off-line purification of the samples of interest, sample introduction to the machine is typically the most rate controlling step. The present invention provides a high-throughput screening method for use with mass spectrometry by providing faster sample purification steps.

The rate of screening is optionally increased beyond that of the autosampler by using pooling strategies, e.g., with the neutral loss, parent ion screening methods described above. A plurality of samples, e.g., similar or related samples, are optionally pooled or mixed together and injected into the mass spectrometer as one sample. The data is then deconvoluted to provide identification or analysis for each of the pooled samples. For example, five different substrates are reacted with an enzyme and the results pooled. The five different substrates may produce five related or similar compounds as products. The products are pooled and analyzed. Neutral loss analysis is then optionally performed on the pooled samples. For example, a specified neutral fragment is removed from all the samples, e.g., in the second quadrupole, and then the data is deconvoluted to determine the parent ion as detected in the first quadrupole to provide results for each of the individual samples.

About 2 to about 1000 samples are optionally pooled, thus increasing the throughput to about 400 samples per hour to about 240,000 samples per hour, e.g., at one injection every 15 seconds. If the speed of the autosampler is increased beyond 1 injection every 15 seconds, even greater screening rates are obtained. Optionally, more samples are pooled to provide greater screening rates. Typically about 5 to about 500 samples are pooled. More typically about 5 to about 100 samples are pooled or about 10 to about 20 samples. At 15 seconds per injection MS rate, the screening rate for pools comprising 100 samples each is about 24,000 samples per hour or about 576,000 samples per day. Typically at least about 500 samples, e.g., cell colonies or library members, at least about 1000 samples, at least about 5000 samples, at least about 10,000 samples, at least about 25,000 samples, or at least about 100,000 samples are screened, e.g., for presence, absence, or activity of one or more component, e.g., non-column-separated components, in less than an hour. In other words, at least about 1000 samples, at least about 25,000 samples, at least about 100,000 samples, or at least about 500,000 samples or more are screened in about 1 day.

VII. Kits

The system described herein is optionally packaged to include many, if not all, of the necessary reagents for performing the preferred function of high throughput mass spectrometry using an off-line parallel purification system. Such kits also typically include appropriate containers and instructions for using the devices and reagents, and in cases where reagents are not predisposed in the devices themselves, with appropriate instructions for introducing the reagents into the cell growth plate or mass spectrometer of the device. Such kits typically include a cell growth plate with necessary reagents predisposed in the wells or separately packaged. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

The discussion above is generally applicable to the aspects and embodiments of the invention described above. Moreover, modifications can be made to the method and apparatus described herein without departing from the spirit and scope of the invention as claimed, and the invention can be put to a number of different uses including the following.

The use of a mass spectrometry system to perform high-throughput screening of enzyme reaction pathways.

The use of a mass spectrometry system as described herein to perform high throughput screening of reactants and or products of enzyme reactions.

The use of a mass spectrometry system as described herein to perform high throughput screening of nucleic acid library.

The use of an off-line parallel purification as described herein to perform high throughput mass spectrometry screening.

The use of an off-line parallel purification as described herein to perform high throughput mass spectrometry screening of enzyme reaction pathways.

An assay utilizing a use of the mass spectrometry system described herein.

EXAMPLES

The following examples are provided by way of illustration only and not by way of limitation. Those of skill will readily recognize a variety of noncritical parameters which could be changed or modified to yield essentially similar results.

Example 1

HTP-MS—Atrazine Production

Atrazine is a member of the family of triazine-derived herbicides. Bacteria from sites contaminated with this widely used herbicide were isolated that were able to metabolize and degrade atrazine. A *Pseudomonas* strain was found to contain a gene encoding atzA, a 473 amino-acid protein that catalyzes the transformation of atrazine to hydroxyatrazine, the first step in the degradation pathway of atrazine (see also, De Souza, M., Sadowsky, M. J. & Wackett, L. P.: Atrazine Chlorohydrolase from *Pseudomonas* sp. Strain ADP: Gene Sequence, Enzyme Purification, and Protein Characterization. *J. Bacteriol.* 178:4894–4900 (1996)) (see also, FIG. 1).

The biochemical degradation of atrazine by the *Pseudomanas* strain sp. ADP is an environmentally sound way of cleaning up contaminated sites. In order to be economically competitive, an increase of the wild type activity of the atza gene was desirable. The atzA gene was cloned into a pUC-derived vector under the control of a lac promoter, and the vector transformed into *E. coli* TG1. The expression of the gene was repressed in presence of glucose and induced with isopropyl thiogalactose (IPTG). The plasmid also contained the gene for Kanamycin resistance.

Library Construction and Cell Growth

The atza gene was shuffled, and the initial library plated onto Kanamycin/2% glucose plates. A robotic colony picker (Q-bot, Genetix) picked all colonies into a microtiter plate of 96 wells containing 2XYT (100 µL) medium with kanamycin and 2% glucose per well. The cells were grown in a specially designed shaker for microtiter plates (Kuehner, Switzerland) at 37° C. overnight. The saturated cultures were diluted 20-fold into 2XYT (100 µL) with Kanamycin and IPTG to initiate expression and grown again overnight at 37° C.

Atrazine Degradation

Cells were harvested by centrifugation and resuspended into 100 µL ammonium acetate (10 mM, pH 7). 5 µL of resuspended cells were transferred into a reaction well containing 100 µL of reaction buffer with atrazine (100 µM) and ammonium acetate (10 mM, pH 7). The reaction proceeded for 6 hours at room temperature under constant shaking. The reaction was quenched by adding an equal volume of methanol (100 µL). The entire reaction mixture was transferred onto a filter plate and any solid cell debris and precipitates removed by filtration. The samples were injected directly into the electrospray mass spectrometer by flow injection and analyzed by tandem mass spectrometry.

MS/MS Method Development

A solution of 1 mM atrazine in acetonitrile was prepared and used to develop a MS/MS method on a triple quadruple mass spectrometer (Finnigan TSQ 7000). The mobile phase was acetonitrile. The collision energy was set to −20 eV.

Figure 2A:
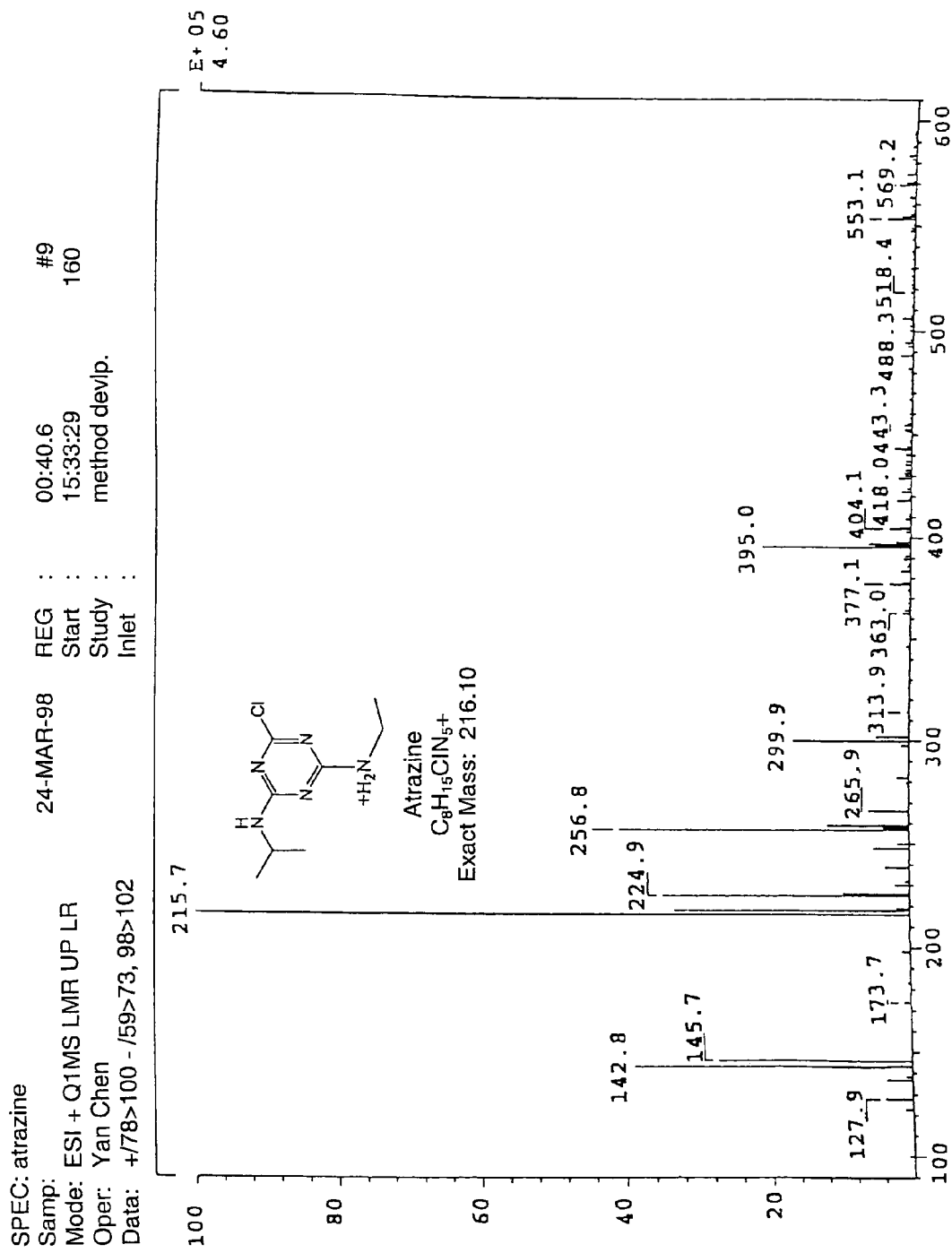
FIG. 2, panels A and B show MS/MS plots of Atrazine.
Figure 2B:
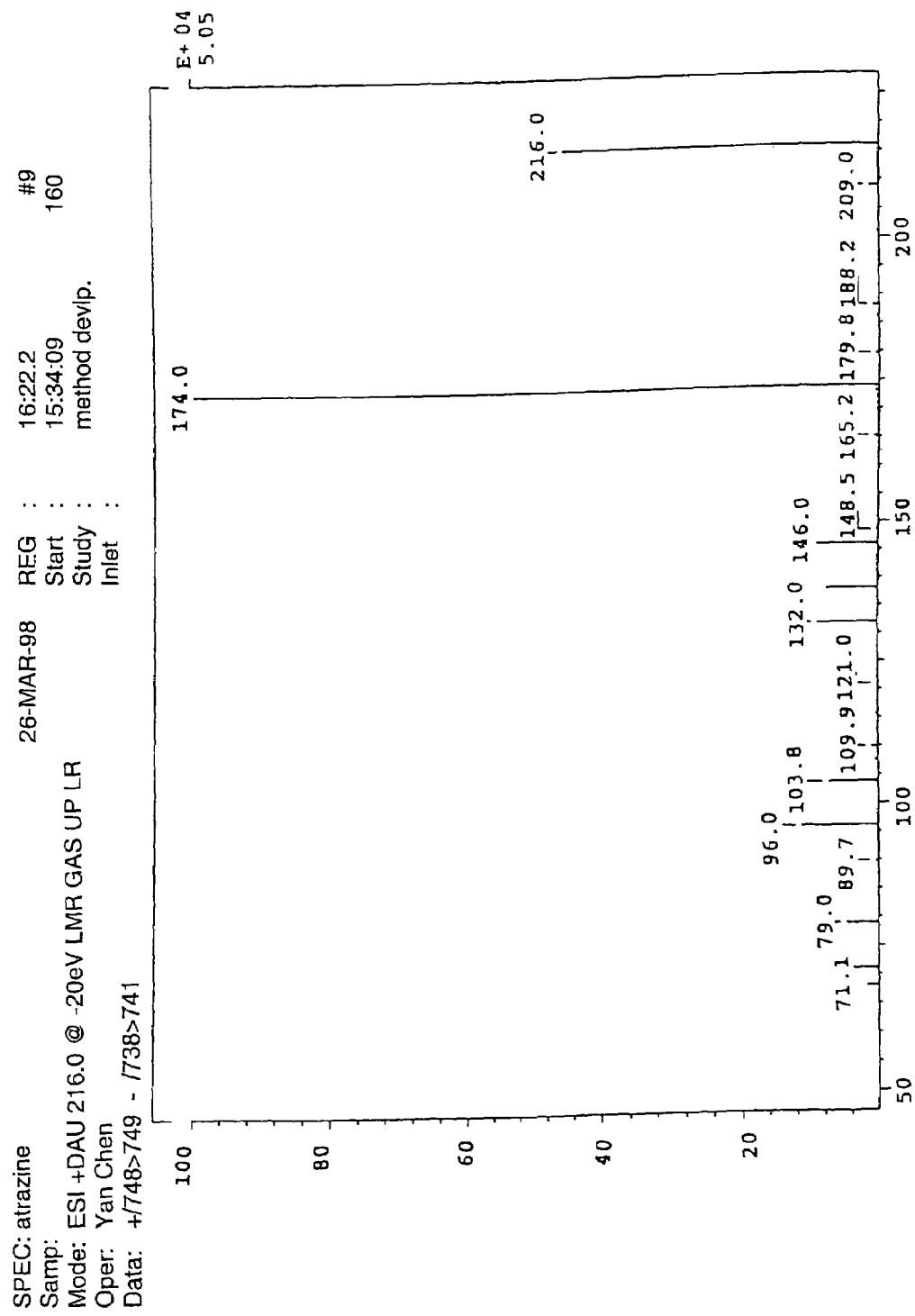

The transition of m/z=216 (parent ion) to m/z=174 (daughter ion) was monitored (see FIG. 2, panels A and B).

MS/MS analysis

Figure 3:
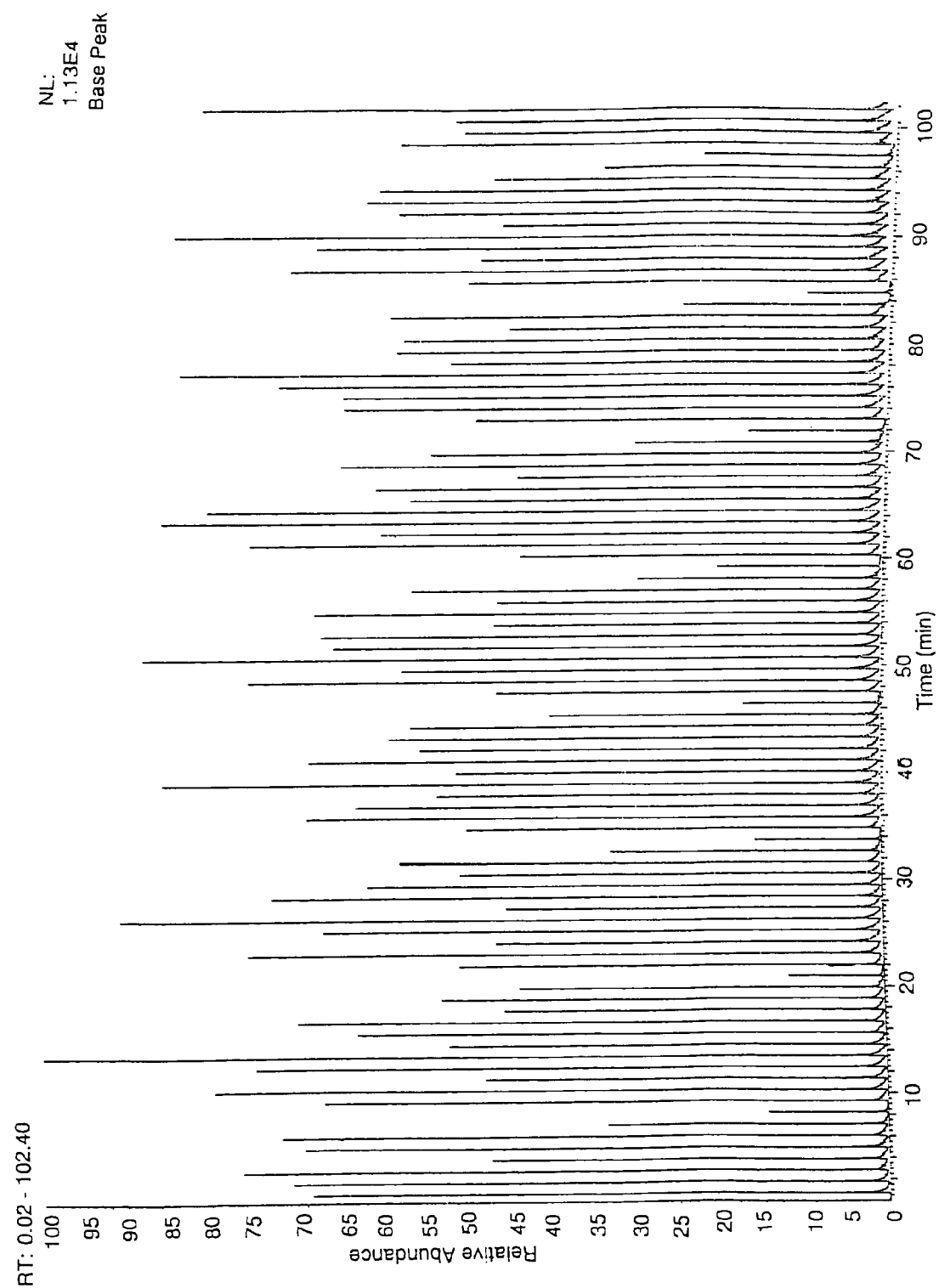
FIG. 3 is a graph showing relative abundance versus time.

FIG. 3 shows results of a typical plate of 96 samples. Each row contains twelve different reaction conditions with various mutants that were reproduced across the eight columns. A periodical pattern of 12 peaks is clearly visible. Bacterial cell growth, reaction and sample workup were performed in parallel fashion as described above.

Materials

Ammonium acetate, glucose and IPTG and Kanamycin were purchased from Sigma. 2XYT medium was prepared according to Sambrook, J., Fritsch, E. F. & Maniatis, T.: *Molecular Cloning, A Laboratory Manual.* Cold Spring Harbor Laboratory Press 1989. Microtiter plates for cell growth were sterile flat-bottom shallow well plates from Nunc. Reactions were performed in 96 well Costar polystyrene V-bottom plates. Filter plates were from Millipore HV 0.45 µm Durapore.

Example 2

High Throughput Screening for Directed Evolution of Enzymes and Pathways Using Mass Spectrometry High throughput chemical screening of enzyme reactions involves quantitative detection of substrate(s) and product(s). The most universal detection method to date is mass spectrometry which allows identification of a particular organic molecule, e.g., based on mass to charge ratio. Electrospray ionization is a mild method of transferring charged polar organic molecules into the gas phase and applicable for most biologically relevant organic molecules.

DNA shuffling technology is used to create a library of related gene sequences that encode enzyme(s) that catalyze chemical reactions. The library of related gene sequences are, e.g., on plasmids that are transformed into bacteria. Typically, a single bacterial clone carries a unique gene sequence representing a unique variant of a particular enzyme or enzyme pathway, although many other shuffling formats are also suitable.

Figure 4:
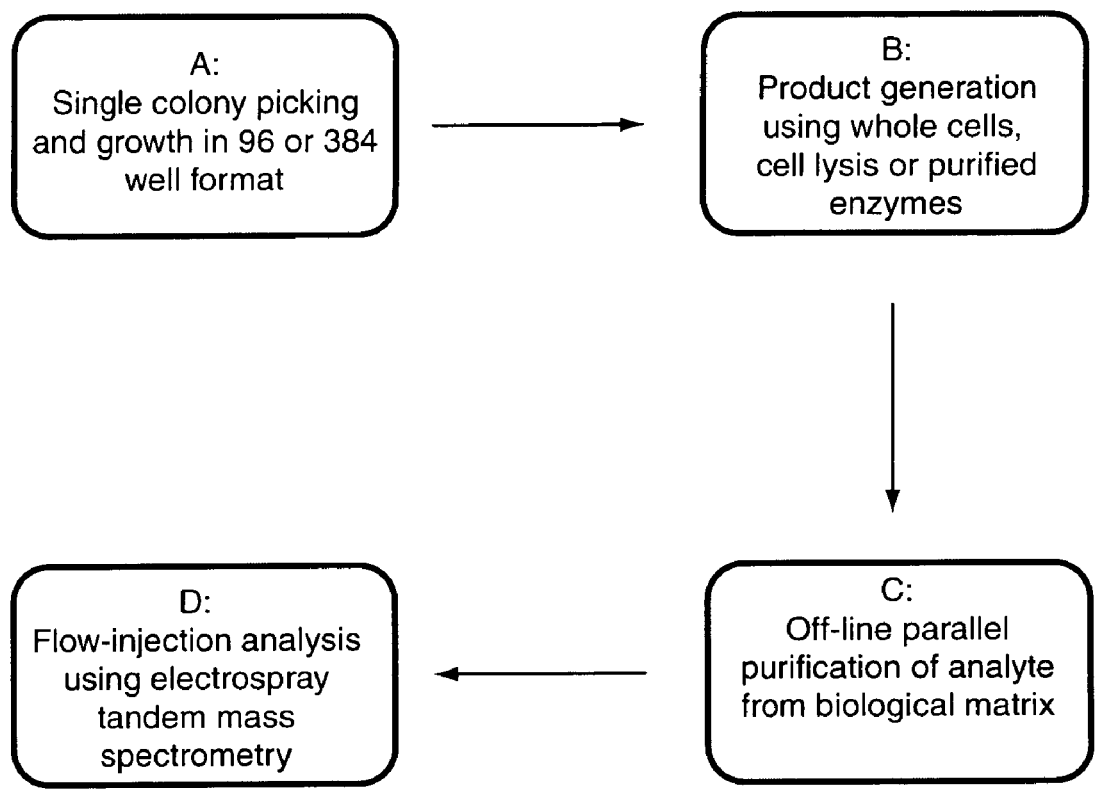
FIG. 4 is a schematic overview of an exemplar high throughput method of the invention.

FIG. 4 describes the steps that are typically used to monitor enzyme reactions by mass spectrometry from a single bacterial colony.

A: Single Colony Picking and Growth in 96 or 384 Well Format

Single colonies are picked directly from transformation plates into 384 or 96-well microtiter plates with appropriate growth media using the Q-bot from Genetix. The maximum speed of the Q-bot is about 4000 colonies per hour. The microtiter plates are incubated in a special plate shaker for cell growth.

B: Product Generation Using Whole Cells, Cell Lysis or Purified Enzymes

Each single colony was grown up in a single microtiter well to uniformity and then treated in several different ways to initiate product formation. If enzyme expression is purposely suppressed during cell growth, which is sometimes desirable, expression can be induced by removing the suppressor or adding activator molecules.

Cells that contain active enzymes are lysed or treated with permeabilizing agents to enable for bulky and/or strongly ionic substrates to penetrate cell walls. This is especially useful for gram-negative bacteria like *E. coli*. Some enzymes are secreted into the media (i.e. if expressed in gram-positive bacteria like *bacillus* with an appropriate signal sequence) in which case no extra treatment is necessary.

In some cases, the enzyme of interest is purified on a purification resin, and the substrate added to the purified proteins. The protein purification step eliminates sample preparation steps noted below (e.g., see C). However, protein purification methods are typically used for single enzyme evolutions and are not as often for pathway evolution.

Initiation of product formation can also be achieved by inoculating the bacterial culture into a different medium. In the above cases, initiation of product formation is performed in a parallel fashion on microtiter plates, e.g., in a 96 or 384 well format.

C: Off-Line Parallel Purification of Analyte from Biological Matrix

There are at least two factors which influence quantitative detection of an analyte in a mass spectrometer. The signal can be suppressed or masked by impurities in the matrix. Also, mass spectrometers are sensitive instruments that are not typically designed for handling crude samples. Strongly ionic buffers and macromolecules like DNA or proteins in the matrix can lead to a reduction in signal and in some cases to clogging of the machine. Therefore, sample cleanup is often beneficial.

Traditionally, crude samples were cleaned on a liquid phase chromatography column prior to introducing them into the machine. Liquid chromatography combined with mass spectrometry (LC/MS) is a useful way to clean crude samples. However, each column run is time consuming, limiting the speed of sample analysis. Flow injection analysis (FIA) is typically rate dependent on the speed of the autosampler, which in current formats ranges from about 30 to about 40 seconds per injection and which is getting faster as newer models of autosamplers are manufactured.

Sample preparation for FIA takes into account steps from reaction with cells to introduction to the mass spectrometer. One factor is to adjust reaction conditions for product formation to accommodate MS compatibility without compromising screening quality. Reaction conditions are typically as close as possible to the target environmental conditions under which these enzymes are used, in order to ensure that the screen is meaningful. These conditions are project dependent. Once the conditions are defined, further sample cleanup is often beneficial. Effective sample cleanup is dependent on the physico-chemical nature of the analyte as well as the matrix.

Several strategies are used to accommodate a variety of different analytes in various biological matrices. A few of these strategies are provided below.

As noted above in Example 1, small molecule substrates with hydrophobic moieties like atrazine penetrate into the *E. coli* cytoplasm without lysis. Using a volatile buffer such as ammonium acetate allowed very simple cleanup. Substrate was added and cell debris filtered off in a parallel fashion.

Small inorganic ion analytes were often masked by coordinating metal ions. Reaction buffers were chosen to reduce the concentration of ionic species to a minimum, and the remaining cations removed by cationic exchange resin.

Oligosaccharide analytes were cleaned by removing all ionic species using a mixed ion exchange resin. Since the cells (*E. coli*) were partially lysed, cell debris, DNA and protein impurities were precipitated with ethanol and removed by filtration.

Hydrophobic molecules like polyketides were extracted from the aqueous phase by organic solvents, which also was an efficient method to remove all ionic impurities.

Sample preparation was adopted to process 96 samples in parallel in a highly automated fashion, thereby ensuring that the screening rate was only dependent on the speed of sequential analysis in the mass spectrometer.

D: FLOW-Injection Analysis on Electrospray Tandem Mass Spectrometer

Triple quadrupole mass spectrometers allow MS/MS analysis of samples. The machine can be set to let one particular parent ion through the first quadrupole which undergoes fragmentation reactions with an inert gas. The most prominent daughter ion can then be singled out in the third quadrupole. This method creates two checkpoints for analyte identification. The particle detected has the correct molecular mass to charge ratio for both the parent and daughter ion. Tandem mass spectrometry thus leads to higher specificity and often also to a higher signal:noise ratio. It also introduced further separation by distinguishing analyte from impurities with same mass to charge ratio.

Flow injection analysis of off-line purified samples using tandem mass spectrometry allowed sample analysis of about 100 samples or more in less than one hour. The throughput limitations were set by the nature of sequential analysis of the mass spectrometer as opposed to parallel analysis of other detection methods (i.e. UV/VIS spectrometers). Sample introduction to the machine was the rate limiting step.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. All patents, patent applications, and publications cited herein are incorporated by reference in their entirety for all purposes.

The invention claimed is:

1. A method of performing high throughput mass spectrometry screening, the method comprising:
   (i) providing cells that have been transfected or transformed with one or more members of a library of related genes;
   (ii) growing the cells in vitro in a biological matrix to express said members of the library of related genes;
   (iii) separating the cells or cell debris thereof from one or more component of interest using centrifugation or filtration in a parallel fashion to provide samples comprising the component(s) of interest;
   (iv) performing flow-injection analysis using electrospray tandem mass spectrometry on the samples from step (iii) to obtain mass-to-charge ratio data for the component of interest,
   wherein the component(s) of interest is selected from the group consisting of an inorganic ion, a secondary metabolite, a protein binding molecule, a carbohydrate, a carbohydrate binding molecule, an enzyme, an enzyme substrate, a product of an enzyme catalyzed reaction, a nucleic acid, and a product of a nucleic acid catalyzed reaction, and
   wherein the component(s) of interest has not undergone chromatographic separation prior to step (iv).

2. The method of claim 1, wherein at least about 100 samples are screened for presence of the one or more component of interest in less than an hour.

3. The method of claim 1, wherein step (iv) comprises performing parent ion mass spectrometry on a triple quadrupole mass spectrometer which comprises:
   (a) scanning the one or more component of interest in a first quadrupole;
   (b) fragmenting the one or more component of interest in a second quadrupole by collision induced dissociation; and,
   (c) scanning a third quadrupole at a specified mass.

4. The method of claim 1, wherein step (iii) comprises using centrifugation.

5. The method of claim 1, wherein step (iii) comprises using filtration.

6. The method of claim 1, wherein an automatic sampler transports samples from step (iii) to the mass spectrometer for injection and analysis at a rate of at least 100 samples an hour.

7. The method of claim 1, wherein the cells are lysed prior to step (iii).

8. The method of claim 1, wherein the cells are permeabilized prior to step (iii).

9. The method of claim 1, wherein the component(s) of interest is obtained from cell supernatant.

10. The method of claim 1, wherein the component(s) of interest is a product of an enzymatic reaction.

11. The method of claim 1, wherein the cells are bacterial cells.

12. The method of claim 1, wherein the cells are eukaryotic cells.

13. The method of claim 1, wherein step (iii) is performed in a volatile buffer, a buffer that reduces concentration of ionic species, or an organic solvent.

14. The method of claim 10, further comprising simultaneously quantifying the amount of the product(s) of the enzymatic reaction and an enzyme substrate.

15. A method of performing high throughput mass spectrometry screening, the method comprising:
   (i) providing cells that have been transfected or transformed with one or more members of a library of related enzyme encoding genes;
   (ii) growing the cells in vitro in a biological matrix to express said members of the library of related enzyme encoding genes;
   (iii) contacting the cells with one or more enzyme substrates to initiate formation of one or more products of an enzymatic reaction;
   (iv) separating the cells or cell debris thereof from the product of the enzymatic reaction and/or enzyme substrate using centrifugation or filtration in a parallel fashion to provide samples comprising the product(s) of the enzymatic reaction and/or enzyme substrate(s); and
   (v) performing flow-injection analysis using electrospray tandem mass spectrometry on the samples from step (iv) to obtain mass-to-charge ratio data for the product(s) of the enzymatic reaction and/or enzyme substrate(s), wherein the product(s) of the enzymatic reaction and enzyme substrate(s) have not undergone chromatographic separation prior to step (v).

16. The method of claim 15, wherein at least about 100 samples are screened for presence of the product(s) of an enzymatic reaction or enzyme substrate(s) in less than an hour.

17. The method of claim 15, further comprising simultaneously quantifying the amount of the product(s) of an enzyme reaction and the enzyme substrate(s).

18. The method of claim 15, wherein step (v) comprises performing parent ion mass spectrometry on a triple quadrupole mass spectrometer which comprises:
   (a) scanning the product(s) of the enzymatic reaction and/or enzyme substrate in a first quadrupole;
   (b) fragmenting the product(s) of the enzymatic reaction and/or enzyme substrate in a second quadrupole by collision induced dissociation; and,
   (c) scanning a third quadrupole at a specified mass.

19. The method of claim 15, wherein an automatic sampler transports the samples from step (iv) to the mass spectrometer for injection and analysis at a rate of at least 100 samples an hour.

20. The method of claim 15, wherein the cells in step (iii) are lysed cells.

21. The method of claim 15, wherein the cells in step (iii) are permeabilized cells.

22. The method of claim 15, wherein the cells are bacterial cells.

23. The method of claim 15, wherein the cells are eukaryotic cells.

24. The method of claim 15, wherein step (iv) comprises using centrifugation.

25. The method of claim 15, wherein step (iv) comprises using filtration.

26. The method of claim 15, wherein step (iv) is performed in a volatile buffer, a buffer than reduces concentration of ionic species, or an organic solvent.

* * * * *